(12) United States Patent
Lambkin-Williams et al.

(10) Patent No.: US 9,833,506 B2
(45) Date of Patent: Dec. 5, 2017

(54) VACCINE—SCREENING METHOD

(71) Applicants: RETROSCREEN VIROLOGY LTD, London (GB); UNIVERSITY OF SOUTHAMPTON, Southampton (GB)

(72) Inventors: Robert Lambkin-Williams, Brighton (GB); John S. Oxford, London (GB); Thomas Wilkinson, Hampshire (GB)

(73) Assignees: HVIVO SERVICES LIMITED, London (GB); UNIVERSITY OF SOUTHAMPTON, Southampton, Hampshire (GB)

( * ) Notice: Subject to any disclaimer, the term of this patent is extended or adjusted under 35 U.S.C. 154(b) by 0 days.

(21) Appl. No.: 14/366,602

(22) PCT Filed: Dec. 21, 2012

(86) PCT No.: PCT/GB2012/053253
§ 371 (c)(1),
(2) Date: Jun. 18, 2014

(87) PCT Pub. No.: WO2013/093512
PCT Pub. Date: Jun. 27, 2013

(65) Prior Publication Data
US 2014/0356388 A1 Dec. 4, 2014

Related U.S. Application Data

(63) Continuation of application No. 13/336,648, filed on Dec. 23, 2011, now abandoned.

(30) Foreign Application Priority Data

Dec. 23, 2011 (GB) ..................... 1122297

(51) Int. Cl.
*A61K 39/145* (2006.01)
*A61K 39/12* (2006.01)
*G01N 33/50* (2006.01)
*C07K 14/005* (2006.01)

(52) U.S. Cl.
CPC ............ *A61K 39/145* (2013.01); *A61K 39/12* (2013.01); *C07K 14/005* (2013.01); *G01N 33/505* (2013.01); *C12N 2760/16122* (2013.01); *C12N 2760/16134* (2013.01); *C12N 2760/16171* (2013.01); *G01N 2500/10* (2013.01)

(58) Field of Classification Search
CPC .......... A61K 2300/00; A61K 2039/505; A61K 39/12; A61K 2039/572; A61K 2039/70; A61K 39/145; A61K 39/00; A61K 38/00; A61L 2300/25; C07K 14/005; C07K 7/06; C07K 7/08; C07K 1/047; G01N 33/6878; G01N 33/6893; B01J 2219/00725; C12N 2770/34022; C40B 40/04; C40B 60/12
See application file for complete search history.

(56) References Cited

U.S. PATENT DOCUMENTS

2010/0285050 A1 11/2010 Gilbert et al.
2013/0164315 A1 6/2013 Lambkin-Williams et al.

FOREIGN PATENT DOCUMENTS

WO WO 98/23960 A1 6/1998
WO WO 99/36568 A2 7/1999

OTHER PUBLICATIONS

Lee et al. (Journal of Clinical Investigation, Oct. 2008, vol. 118, No. 10. pp. 3478-3490).*
Lecher et al. J. Exp. Med. 2000, vol. 191, No. 9, pp. 1499-1512.*
Chisari Francis Annu. Rev. Immunology 1995, vol. 13, pp. 29-60.*
Aurille et al. Human Immunology 2009, Sep. 70 (9), pp. 711-721.*
Zinckgraf et al. Vaccine 2009, vol. 27 (39), pp. 5397-5401.*
Lee et al. JCV, published on line Sep. 18, 2008, pp. 3478-3490.*
Menne et al. Journal of Virology, 1998, vol. 72, No. 7, pp. 6083-6091.*
A. Eshofonie et al: "An adaptation of recombinant vaccinia-based ELISPOT and intracellular cytokine staining for a comparative measurement of cellular immune responses in HIV-1 and HIV-2 infections in West Africa", Clinical & Experimental Immunology, vol. 146, No. 3, Dec. 1, 2006 (Dec. 1, 2006), pp. 471-478.
Fonseca Simone G et al: "Identification of novel consensus CD4 T-cell epitopes from Glade B HIV-1 whole genome that are frequently recognized by HIV-1 infected patients", AIDS (Hagerstown),vol. 20, No. 18, Nov. 2006 (Nov. 2006), pp. 2263-2273.
Bercovici N et al: "New methods for assessing T-cell responses.", Clinical and Diagnostic Laboratory Immunology Nov. 2000, vol. 7, No. 6, Nov. 2000 (Nov. 2000), pp. 859-864.
Hickman C J et al: "Use of Synthetic Peptides to Identify Measles Nucleoprotein T-Cell Epitopes in Vaccinated and Naturally Infected Humans", Virology, Elsevier, Amsterdam, NL, vol. 235 No. 2, Sep. 1, 1997 (Sep. 1, 1997), pp. 386-397.
Tom M Wilkinson et al: "Preexisting influenza-specific CD4+ T cells correlate with disease protection against influenza challenge in humans", Nature Medicine, vol. 18, No. 2, Jan. 29, 2012 (Jan. 29, 2012), pp. 274-280.
Corbet S et al: "Optimization and immune recognition of multiple novel conserved HLA-A2, human immunodeficiency virus type 1-specific CTL epitopes", Journal of General Virology, Society for General Microbiology, Spencers Wood, GB, vol. 84, No. 9, Sep. 1, 2003 (Sep. 1, 2003), pp. 2409-2412.

(Continued)

*Primary Examiner* — Bao Li
(74) *Attorney, Agent, or Firm* — Mintz Levin Cohn Ferris Glovsky and Popeo, P.C.; Muriel Liberto, Esq.

(57) ABSTRACT

The present invention provides screening methods which may be regarded as in vitro or ex vivo methods of interrogating the immune system to understand what viral antigens are "seen" and responded to by T cells of the immune systems during viral infection. The screening methods further link in vitro or ex vivo responses to progression of infection in subjects.

20 Claims, 12 Drawing Sheets

(56) References Cited

OTHER PUBLICATIONS

M. Altfeld et al: "Enhanced Detection of Human Immunodeficiency Virus Type 1-Specific T-Cell Responses to Highly Variable Regions by Using Peptides Based on Autologous Virus Sequences", Journal of Virology, vol. 77, No. 13, Jul. 1, 2003 (Jul. 1, 2003), pp. 7330-7340.
Database UniParc [Online] EMBL; (Jan. 20, 2011), XP002713240, Database accession No. G9K136 the whole document.
International Search Report of PCT/GB2012/053253, dated Oct. 2, 2013.
Gianfrani, C. et al.(May 2000). "Human Memory CTL Response Specific for Influenza A Virus is Broad and Multispecific." *Hum. Immunol.* 61(5):438-452.
Kreijtz, J.H. et al. (Jun. 2008, e-published Mar. 19, 2008). "Cross-Recognition of Avian H5N1 Influenza Virus by Human Cytotoxic T-Lymphocyte Populations Directed to Human Influenza A Virus." *J. Virol.* 82(11):5161-5166.

\* cited by examiner

FIG. 1

VACCINE—SCREENING METHOD

FIELD OF THE INVENTION

The present invention relates to a screening method, and has particular reference to a method of screening peripheral blood against a peptide or a library of peptides to identify peptides that may give rise to an enhanced memory T cell response. Advantageously the T cell response is a $CD4^+$ T cell response. The invention also provides peptides that can be used to provoke an enhanced memory T cell response for use in the treatment or prophylaxis of a viral infection, especially in patients who are immunologically naïve to the virus. The invention further comprehends peptide-based vaccine compositions comprising such peptides and the use of such peptides and vaccine compositions in the treatment or prevention of influenza and other infections.

BACKGROUND TO THE INVENTION

Despite widespread vaccination initiatives, influenza remains a major cause of mortality and morbidity. Each year between 250 000 and 500 000 deaths are attributed to seasonal influenza with associated annual healthcare costs of $14 billion in the US alone. Vaccination programmes aim to minimise the burden of seasonal influenza, with the majority of vaccines available at the time of writing designed to generate protective antibody-mediated immunity. This serological protection is highly strain specific, especially if generated using killed virus preparations. The success of seasonal vaccination programmes is dependent upon both the reliable predictive modelling of strain circulation and the lack of viral coat protein mutation enabling immune evasion during a flu season.

Furthermore, influenza can extend beyond its usual seasonal impact by shifting its antigenic profile significantly enough to escape from protective immunity on a global scale. If such pandemic strains carry traits of high virulence and pathogenicity then associated mortality can be devastating, as seen in the 1918 outbreak.

Influenza viruses can evade established protective immune responses by two distinct mechanisms: The gradual antigenic drift of viral surface epitopes results from low fidelity viral replication and adoption of mutations which eventually allows escape from established serological immunity. Less common, but with significant impacts on global health, is the emergence of entirely new viral strains arising from the reassortment of influenza virus RNA from different strains in a common host. The emerging novel pathogen can result in a pandemic where the new flu strain can spread rapidly through communities which lack protective immunity to novel viral proteins.

In the context of these events where there are no pre-existing protective antibodies, T cells may mediate protection or limit the severity of influenza associated illness (Kreijtz J H et al., Vaccine 25 612-620 2007). Pre-existing T cell responses have been shown to modulate influenza severity in the context of existing antibodies (McMichael et al., N Engl J Med 309, 13-17, 1983) but the role of protective cell mediated immunity (CMI) in sero-negative individuals naïve to a particular flu strain is not understood.

Lee et al. (J Clin Invest 118, 3478-3490, 2008) showed that memory T cells established by seasonal human influenza A infection cross-react with avian influenza A (H5N1) in healthy individuals. However, the experiments were carried out ex vivo and do not necessarily accurately reflect the clinical picture.

Despite of these reports, at the time of writing the main focus of research remains the search for a 'super-antibody' that is capable of targeting all known subtypes of the influenza A virus.

In July 2011, Corti et al. (Science 28 Jul. 2011: 1205669) reported on the isolation of a neutralising monoclonal antibody that recognised the hemagglutinin (HA) glycoprotein of all 16 known subtypes of influenza A and neutralised both group 1 and group 2 influenza A viruses using a single-cell culture method for screening large numbers of human plasma cells. Passive transfer of this antibody conferred protection to mice and ferrets. Complexes with HAs from the group 1 H1 and the group 2 H3 subtypes analysed by x-ray crystallography showed that the antibody bound to a conserved epitope in the F subdomain. Based on these results, it was reported that the antibody may be used for passive protection and to inform vaccine design because of its broad specificity and neutralization potency.

Announcing these findings, Dr A. Lanzavecchia, who led the study, also opined that approaches to developing a universal vaccine that did not rely on antibodies were unlikely to work (report in The Independent, 29 Jul. 2011).

Nevertheless, there remains a need in the art for new therapeutic agents, and methods for identifying such agents, for use in the treatment viral infections, including influenza A, especially in patients who do not have pre-existing protective antibodies for the strain of virus that is the cause of the infection.

SUMMARY OF THE INVENTION

The present inventors have identified a role for memory T cells that recognise particular viral antigens in limiting disease severity in viral infections. This effect led the present inventors to develop a screening method for identifying peptides that can manipulate T cell memory into recognising viral antigens. Peptides having the desired effect have been identified and these peptides may therefore be useful in the preparation of a vaccine composition.

A first aspect of the present invention is a screening method which may be regarded as an in vitro or ex vivo method of interrogating the immune system to understand what viral antigens are "seen" and responded to by T cells of the immune system during viral infection. This screening method enables identification and demonstration of peptides which are important in driving T cell responses. Correlation of those T cell responses with reduction in disease severity allows confirmation of disease protection.

In a first aspect the present invention provides a screening method for identifying a peptide capable of inducing a T cell response, comprising:
a) contacting a peptide having a level of identity with a sequence of a protein of a virus, with a test sample comprising T cells obtained from blood from a subject who is currently infected or has been recently infected with the virus,
b) quantifying the response of the T cells to the peptide,
c) comparing the T cells' response in b) to a response of a control sample comprising T cells obtained from blood from a subject who is not currently infected nor been recently infected with the virus, when contacted with the peptide,
wherein a greater response to the peptide in b) than in c) is indicative of a peptide capable of inducing a T cell response.

Induction of a T cell response indicates that the peptide is capable of inducing T cell immunity to the virus. T cell immunity to the virus means these T cells are capable of reducing symptoms of a viral disease. For example, CD4+ T cells induced by influenza peptides are useful in reducing symptoms of influenza. Therefore, a peptide identified as inducing a T cell response can be used to reduce symptoms of a viral infection.

The first aspect of the present invention also provides a screening method for identifying a peptide capable of inducing a T cell response and inducing T cell immunity comprising:
a) contacting a plurality of peptides having a level of identity with a sequence of a protein of a virus, with a plurality of test samples comprising T cells obtained from blood from subjects who have been inoculated with the virus and are currently or have been recently infected with the virus,
b) quantifying the response of the T cells to the peptides,
c) comparing the T cells' response in b) to responses of control samples comprising T cells obtained from blood from a subjects who have not been inoculated and is not currently infected nor been recently infected with the virus, when contacted with the peptide,
wherein a greater response to the peptide in b) than in c) is indicative of a peptide capable of inducing a T cell response,
d) obtaining a marker of progression of infection in the inoculated subjects, and
e) correlating the marker of progression of infection with T cell responses
wherein such a correlation indicates that the peptide which caused the T cells response can induce T cell immunity.

In an alternative embodiment a first aspect of the present invention provides a screening method for identifying a peptide capable of inducing a T cell response and inducing T cell immunity to a virus, the method comprising:
a) placing a plurality of test subjects who are not currently infected nor recently been infected with the virus into controlled conditions in isolation,
b) collecting a control sample comprising T cells from the subjects,
c) inoculating the test subjects with the virus,
d) obtaining a marker of progression of infection in the test subjects,
e) collecting a test sample comprising T cells from the test subjects,
f) contacting a plurality of peptides having a level of identity with a sequence of a protein of the virus with T cells obtained from the control sample and quantifying the response of the T cells to the peptide,
g) contacting the peptides with T cells obtained from the test samples and quantifying the response of the T cells to the peptides,
h) comparing the T cell responses in f) and g), wherein a greater response to the peptide in g) than in f) is indicative of a peptide capable of inducing a T cell response,
i) identifying a correlation between the marker of progression of infection obtained at d) and the T cell responses obtained at g)
wherein such a correlation indicates a peptide useful in inducing T cell immunity to the virus.

Preferably the test sample is obtained at a known time point after inoculation with the virus, for example, 1-28 days, 2-20 days, 3-15 days, 5-10 days, most preferably 7 days post inoculation.

A second aspect of the present invention is a screening method which may be regarded as an in vitro or ex vivo method of interrogating the immune system to find pre-existing native T cell responses to potential viral antigens, which enable a subject to experience less severe symptoms should they become infected with a virus. This screening method also enables identification and demonstration of peptides which are important in driving T cell responses.

In a second aspect, the present invention therefore provides a use of a peptide in a method of screening to identify a peptide capable of ameliorating a viral infection comprising:
a) contacting a peptide having a level of identity with a sequence of a protein of a virus, with a test sample comprising T cells obtained from blood from a subject,
b) quantifying the response of the T cells to the peptide,
wherein an above background response is indicative of a peptide capable of inducing a T cell response and therefore ameliorating a viral infection.

The detection of a T cell response indicates that the peptide is capable of inducing T cell immunity to a virus.

In preferred embodiments, the test sample comprising T cells is obtained from blood from a subject who is subsequently inoculated and infected with the virus. The subsequent inoculation and infection occurs under controlled conditions in isolation.

The second aspect of the present invention also provides a screening method for identifying a peptide capable of ameliorating a viral infection, comprising:
a) contacting a plurality of peptides having a level of identity with a sequence of a protein of a virus, with a plurality of T0 test samples comprising T cells obtained from blood from subjects who are subsequently inoculated and infected with the virus,
b) quantifying the response of the T cells to the peptides, wherein an above background response is indicative of a peptide capable of inducing a T cell response and therefore ameliorating a viral infection, and
c) obtaining a marker of progression of infection in the inoculated subjects, and
d) correlating the marker of progression of infection with T cell responses
wherein such a correlation indicates that the peptide which caused the T cells response can induce T cell immunity.

In an alternative embodiment a second aspect of the present invention provides a screening method for identifying a peptide capable of ameliorating infection by a virus, the method comprising:
a) placing a plurality of test subjects who are not currently infected nor recently been infected with the virus into controlled conditions in isolation,
b) collecting T0 test samples comprising T cells from the subjects,
c) inoculating the test subjects with the virus,
d) obtaining a marker of progression of infection in the test subjects,
e) contacting a plurality of peptides having a level of identity with a sequence of a protein of a virus with T cells from the T0 test samples and quantifying the response of the T cells to the peptides, wherein an above background response is indicative of a peptide capable of inducing a T cell response, and
f) identifying a correlation between the marker of progression of infection obtained at d) and the T cell responses obtained at e) wherein such a correlation indicates a peptide useful in ameliorating infection by the virus.

Ameliorating a viral infection may be reducing symptoms of viral infection, ameliorating or reducing illness, or reducing or ameliorating a disease caused by a virus.

Optionally the test subjects in the first and second aspects of the invention have not been vaccinated against the virus.

Advantageously in the first and second aspects of the present the marker of progression of infection is
i) a score of severity of symptoms of the viral infection experienced by the subjects and optionally an inverse correlation between symptom scores and T cell responses is identified,
ii) a measure of viral shedding in the test subjects and optionally an inverse correlation between viral shedding and T cell responses is identified,
iii) duration of illness experienced by the test subjects and optionally an inverse correlation between duration of illness and T cell responses is identified,
iv) a measure of a biomarker typically increased during infection with the virus and optionally an inverse correlation between the biomarker and the T cell responses is identified, or
v) a measure of a biomarker typically decreased during infection with the virus and optionally a positive correlation between the biomarker and the T cell responses is identified.

In the first and second aspect of the present invention the peptide is generally about 7 to about 25 amino acids long, optionally 9-25 amino acids long or 10-20 amino acids long and preferably about 15, 16, 17 or 18 amino acids long.

In the first and second aspect of the present invention the level of identity the peptide has with a sequence of a protein of a virus conveniently is at least 70% identity. In embodiments the peptide may have 80%, 90% or 95% identity. In further embodiments the peptide has an identical sequence with a sequence of a viral protein.

In the screening methods of the first and second aspect of the present invention, advantageously a library of peptides is used. The library may substantially span a protein of a viral proteome. Preferably the library of peptides substantially spans the conserved proteins of the viral proteome. Optionally the library of peptides substantially spans the viral proteome.

The screening methods of the present invention allow selection of one or more peptides from a library of peptides which can induce T cell responses and which therefore may be used to reduce the symptoms of a viral infection.

Conveniently the peptide may be synthetic.

The screening methods of the first and second aspect of the present invention are applicable for the investigation of T cell responses to peptides having a level of identity with any infectious virus. The virus may be a respiratory virus, such as an influenza virus, rhinovirus or respiratory syncytial virus. In particular, the virus may be an influenza virus and can be influenza A.

The influenza A virus genome encodes eleven proteins. These are hemagglutinin (HA), neuraminidase (NA), nucleoprotein (NP), matrix proteins M1 and M2, two non-structural proteins NS1 and NEP, PA, and polymerases PB1, PB 1-F2, and PB2. HA and NA appear on the virion surface and are highly diverse. The core proteins are more conserved between different influenza viruses. Suitably a peptide of the present invention may have a sequence that is derived from a part of the influenza proteome that is conserved between different strains of influenza A, such as a core protein of influenza. Core proteins include NP, M1, M2, NS1, NEP, PA, PB1, PB1-F2 and PB2, For instance, the peptides of the present invention may be derived from matrix (M1 or M2), nucleoprotein (NP) or polymerase (PB1 or PB2) proteins, because these proteins are subject to less mutation than the proteins of the viral coat. Peptides derived from matrix (M1 or M2) or nucleoprotein (NP) are particularly preferred.

Advantageously the subject from whom the test sample comprising T cells is obtained is seronegative for the virus prior to infection. Preferably, the subject has no current or recent viral infection. The subject may remain in controlled conditions optionally in isolation. This can be useful to control the viral or other infectious agents with which the subject comes into contact.

Advantageously the test sample is obtained at a known time point after inoculation.

The severity of the symptoms displayed by the subject in response to infection with the virus may quantified. Depending on the virus concerned a variety of different objective or quasi-objective methodologies are available to the person skilled in the art for this. For instance, in the case of influenza one or more of the following symptoms may be scored.

The present inventors have developed a symptom scoring methodology similar to the Jackson score (Jackson et al 1958) and have previously published work based on this (DeVincenzo et al., 2010a; DeVincenzo et al., 2010b; Jackson et al., 1958; Jones et al., 2009; Zaas et al., 2009). In summary, twice daily volunteers complete a diary card on which they rate their symptoms on a four point scale from 0 to 3 corresponding to absent to severe.

The symptoms assessed may be one or more nasal stuffiness, runny nose, sore throat, cough, sneezing, ear ache/pressure, breathing difficulty, muscle aches, fatigue, headache, feverish feeling, hoarseness, chest discomfort and overall discomfort. A total symptom score for a day may be obtained by adding the individual symptom scores for a particular day's morning and evening sessions. The individual symptoms may be divided into three subgroups: system symptoms (muscle aches, fatigue, headache and fever), upper respiratory symptoms (nasal stuffiness, ear ache/pressure, runny nose, sore throat and sneezing) and lower respiratory symptoms (cough, breathing difficulty, hoarseness and chest discomfort). Oral temperatures can also be measured daily, for example 2, 3 or 4 times a day. Fever may be considered to be an oral temperature >37.7° C.

Therefore, for any viral infection a subject or the supervising medical practitioner can score one or more symptoms experienced during the infection. The one or more symptoms to be assessed depend on the specific viral infection. Scoring may occur daily, twice daily or at other convenient intervals. Score cards can be generated for the use of the subjects.

It has been found that there is a correlation between reduced severity of symptoms in a subject infected with a virus and induced or pre-existing T cell immunity.

The methods of the first aspect of the present invention can further comprise a step d) of correlating the severity of the symptoms experienced by the subject from whom the test sample was obtained, with the magnitude of the T cell responses quantified in step b). Wherein a correlation between reduced symptom scores and T cell responses indicates that the peptide which caused the T cells response can induce T cell immunity. (Alternatively phrased an inverse correlation between symptom scores and T cell responses indicates that the peptide which caused the T cell response can induce T cell immunity) The methods of the second aspect of the present invention can further comprise a step c) of correlating the severity of the symptoms experienced by the subject from whom the test sample was obtained and who was subsequently inoculated and infected with the virus with the T cell responses in b). Wherein a correlation between reduced symptom scores and T cell responses indicates that the subject's symptoms were reduced due to the pre-existing T cells which were capable of responding to the peptide, and that that peptide can induce T cell immunity.

In some embodiments, the T cell response to the peptide in a plurality of samples from different subjects may be quantified. Optionally test and control samples comprising T cells are obtained from more than one subject. For example, the method requires samples from more than 5, 6, 7, 8, 9, 10, 12, 15 or 20 subjects. Suitably blood samples from at least 10-20 and preferably samples from 20 to 30 or more subjects are required. This is because humans have a variety of different MHC subtypes and individuals will process different peptides in different ways. Optionally, subjects can be MHC typed prior to inoculation and infection to ensure a spread of MHC subtypes representative of the subject population. The present invention seeks to identify peptides that are useful in inducing a T cell response across a population of subjects. Preferably T cell responses to peptides and optionally correlation to reduced symptom scores allows identification of peptides which reduce symptoms of viral infection across a population of subjects. Therefore it is useful for a vaccine to contain peptides that would be effective for a range of individuals.

In a third aspect, the invention provides a peptide obtainable by the methods described herein. This aspect of the invention also provides a peptide having a sequence that is at least 70% identical to a sequence found within the proteome of a virus and which provokes a T cell response in a sample comprising T cells obtained from blood. Preferably a peptide obtainable by the present methods is capable of reducing symptoms in a subject infected by a virus. Therefore such a peptide is useful in protecting against a viral disease.

A peptide of the invention may therefore have a sequence that is at least 70% identical to a sequence found natively in the influenza proteome, for example the influenza A viral proteome, that is capable of provoking a CD4$^+$ T cell response, and suitably the peptide may have a sequence that is derived from a part of the viral proteome that is conserved between different strains of influenza A. Preferably a peptide of the present invention is capable of reducing symptoms of influenza experienced by a subject.

Other features of peptides described for use in the screening methods are applicable to the peptides of this aspect of the invention.

In a fourth aspect, the present invention provides a vaccine composition comprising at least one peptide in accordance with the invention for use in medicine.

In view of its ability to provoke a T cell response having a magnitude that correlates inversely to the severity of symptoms associated with an infection or other condition that is mediated by the virus, as disclosed below, the peptide of the invention may be used in a method of treatment or prophylaxis of a viral infection or other condition in a human or non-human animal.

Accordingly the invention extends to the use of at least one peptide according to the invention in the preparation of a medicament for the prophylaxis of influenza infection.

The vaccine composition of the invention may be useful in the prevention (or prophylaxis) of influenza.

In a fifth aspect, the invention comprehends a method of treatment or prophylaxis of a disease or condition in a human or non-human subject in need thereof, comprising the step of administering a therapeutically or prophylactically effective amount of the vaccine composition of the invention to the subject. Said disease or condition may be influenza A.

This aspect of the invention also comprehends generating an immune response against influenza in a human or non-human animal subject by administering to said subject a prophylactically effective amount of the vaccine composition of the invention. The immune response may be a prophylactic immune response that either prevents the subject from developing influenza altogether or at least reduces the severity of the symptoms of influenza in the subject.

The terms "prevention" and "prophylaxis" are used interchangeably herein. Prophylaxis of includes both the complete prevention of any disease symptoms developing and the development of milder symptoms of the disease than would otherwise have been the case without the vaccination. The vaccine composition of the invention can therefore be used for example to cause a less severe influenza illness than would have been the case without the vaccination. The vaccine composition of the invention can in other words be said to immunise a subject against influenza.

DETAILED DESCRIPTION OF THE INVENTION

The present invention provides methods for identifying peptides that induce T cell responses in vitro and which may ameliorate how ill a subject infected with a virus feels.

As noted above, a first aspect of the present invention is a screening method which may be regarded as an in vitro or ex vivo method of interrogating the immune system to understand what viral antigens are "seen" and responded to by T cells of the immune system during viral infection to enable a subject to experience less severe symptoms when becoming infected with a virus. The first aspect of the present invention is concerned with the T cell responses which are induced during viral infection and which help ameliorate the viral infection. Also, as noted above, a second aspect of the present invention is a screening method which may be regarded as an in vitro or ex vivo method of interrogating the immune system to find pre-existing T cell response potential to viral antigens, which enable a subject to experience less severe symptoms when becoming infected with a virus. The second aspect of the present invention is concerned with the pre-existing T cell responses which help ameliorate the viral infection.

Some previous studies have obtained T cells from healthy volunteers and investigated the responses of the T cells in vitro to viral peptides. Other studies have obtained T cells from volunteers who were suffering or had recently suffered from a viral infection and investigated the responses of the T cells in vitro to viral peptides. However, these approaches have drawbacks. Due to the complexity of the human immune system, identifying in vitro T cell responses caused by contacting T cells with a specific peptide does not necessarily identify an antigenic peptide that is effective in humans to induce an immune response and reduce severity of disease. The complexity of the human immune system, for example, means that in vivo certain peptides can be processed preferentially to others and this may not be detected in in vitro experiments. Furthermore, nor do studies using animal models necessarily give clinically useful information about human immune responses to antigenic peptides because of the differences between animal and human immune systems. Consequently, the present invention also links T cell responses to a peptide identified in vitro with the severity of disease symptoms experienced by the subject from whom T cells were obtained. The present invention may also link T cell responses to peptides identified in vitro with how ill subjects are during viral infections, for example, the severity of disease symptoms experienced by the subject from whom T cells were obtained. This linkage is possible because the methods of the present invention require T cells to have been obtained from a subject whose time of inoculation and infection is known and whose disease progression is monitored. The disease progression is monitored by obtaining a marker of disease progression, such asscoring the severity of their symptoms. Comparing the T cell responses to a peptide which were detected in vitro, with the how ill a subject felt provides an extra layer of knowledge that has not been achieved before.

The methods of the present invention may provide a further advantage in that the responses elicited and identified are those which are raised in and experienced by a subject as in a natural infection. Vaccination of subjects during or prior to a study can skew results so that T cell responses identified are likely to be directed to the peptides present in a vaccine rather than directed to the peptides to which the immune system naturally responds.

Those identified peptides or viral antigens can be used to induce cell mediated immunity to that viral infection. Additionally peptide sequences that are similar (for example having 70% identity or greater) to those identified viral peptide sequences may also be useful to induce cell mediated immunity to viral infection.

Additionally or alternatively the screening method itself can employ peptides which are similar (for example having 70% identity or greater) to viral peptides and are capable of inducing cell mediated immunity.

The peptide of the third aspect of the invention may be obtainable by the screening method of the first or second aspects.

Cell mediated immunity is an immune response that does not involve antibodies, but instead involves the activation of macrophages, natural killer cells (NK), antigen-specific cytotoxic T-lymphocytes (T cells), and the release of various cytokines in response to an antigen. Activated antigen-specific cytotoxic T cells can induce apoptosis in body cells displaying epitopes of foreign antigen on their surface, such as virus-infected cells.

Following a viral infection, memory T cells, a subset of infection fighting T cells, persist. At a subsequent encounter with the same virus, pre-existing memory T cells play a key role in the immune response to the virus. Memory T cells enable a faster and stronger immune response to be mounted, resulting in an infection which is of shorter duration and with less severe and/or with a reduced number of symptoms.

The inventors have demonstrated (see below) that pre-existing memory T cells responding to viral peptides reduce the severity and duration of a viral illness. The screening methods of the present invention are for identifying peptides which induce a T cell response. A T cell response is indicative of inducing T cell immunity. T cells of use in the present invention can be CD3+ T cells. Therefore a peptide which induces a T cell response may be useful for inclusion in a vaccine against the virus from which they are derived.

The present invention is concerned with the cellular response. T cells which respond to peptide antigens can be CD3+ T cells, including CD4+ and/or CD8+ T cells. After a viral infection a subset of the activated T cells will persist as memory T cells. Therefore the memory T cells can be CD4+ and/or CD8+ T cells. When the virus in question is influenza, the preferred T cell response is from CD4+ T cells and pre-existing memory CD4+ T cells may be more effective than pre-existing memory CD8+ T cells in reducing symptom severity in an influenza infection. When an alternative virus is considered the preferred T cell response can be from CD8+ T cells, or from a combination of CD4+ and CD8+ T cells.

As used herein, the term "peptide" refers to a short sequence of amino acids and includes oligopeptides and polypeptides. These terms are therefore used interchangeably herein. A peptide for use in the first aspect of the invention may have a length in the range of from about 5 to 50 amino acids, typically from about 5 to 40, more typically from about 8 to 30 and more typically from about 9 to 22 amino acids, for example from about 10 to 20 amino acids, although these lengths are not intended to be limiting. In some embodiments the peptide may have a length of from 5, 6, 7, 8, 9 or 10 amino acids up to 11, 12, 13, 14, 15, 16, 17 or 18 consecutive amino acids.

It is envisaged that, in use, a plurality of peptides will be investigated via the screening method the present invention. The peptide to be screened can be a member of a library of peptides. A library of peptides is also referred to interchangeably herein as a peptide library. Typically, a library of peptides contains a large number of peptides, for example many hundreds or thousands of peptides, for example from 100 to 10000 peptides, typically from 200 to 5000 peptides, more typically from 500 to 1000 peptides, for example 550 to 600 peptides and these peptides typically have a systematic combination of amino acids.

In some embodiments, the library of peptides may be a library of peptides in which each peptide has a sequence that is at least 70% identical to a respective sequence taken from the same at least one viral protein. In some embodiments the peptide may be at least 80% or 90% identical to the native sequence; and in some embodiments the peptide may have at least 95% identity to the corresponding sequence in the viral protein. The peptide may have the same sequence as in the viral protein.

"Identity" as known in the art is the relationship between two or more polypeptide sequences or two or more polynucleotide sequences, as determined by comparing the sequences. In the art, identity also means the degree of sequence relatedness between polypeptide or polynucleotide sequences, as the case may be, as determined by the match between strings of such sequences. While there exist a number of methods to measure identity between two polypeptide or two polynucleotide sequences, methods commonly employed to determine identity are codified in computer programs. Preferred computer programs to determine identity between two sequences include, but are not limited to, GCG program package (Devereux, et al., Nucleic Acids Research, 12, 387 (1984), BLASTP, BLASTN, and FASTA (Atschul et al., J. Molec. Biol. 215, 403 (1990)).

One can use a program such as the CLUSTAL program to compare amino acid sequences. This program compares amino acid sequences and finds the optimal alignment by inserting spaces in either sequence as appropriate. It is possible to calculate amino acid identity or similarity (identity plus conservation of amino acid type) for an optimal alignment. A program like BLASTx will align the longest stretch of similar sequences and assign a value to the fit. It is thus possible to obtain a comparison where several regions of similarity are found, each having a different score. Both types of identity analysis are contemplated in the present invention.

The percent identity of two amino acid sequences or of two nucleic acid sequences is determined by aligning the sequences for optimal comparison purposes (e.g., gaps can be introduced in the first sequence for best alignment with the sequence) and comparing the amino acid residues or nucleotides at corresponding positions. The "best alignment" is an alignment of two sequences which results in the highest percent identity. The percent identity is determined by the number of identical amino acid residues or nucleotides in the sequences being compared (i.e., % identity=number of identical positions/total number of positions×100).

The determination of percent identity between two sequences can be accomplished using a mathematical algorithm known to those of skill in the art. An example of a mathematical algorithm for comparing two sequences is the algorithm of Karlin and Altschul (1990) Proc. Natl. Acad. Sci. USA 87:2264-2268, modified as in Karlin and Altschul (1993) Proc. Natl. Acad. Sci. USA 90:5873-5877. The NBLAST and XBLAST programs of Altschul et al. (1990) J. Mol. Biol. 215:403-410 have incorporated such an algorithm. BLAST nucleotide searches can be performed with the NBLAST program, score=100, wordlength=12 to obtain nucleotide sequences homologous to nucleic acid molecules of the invention. BLAST protein searches can be performed with the XBLAST program, score=50, wordlength=3 to obtain amino acid sequences homologous to protein molecules of the invention. To obtain gapped alignments for comparison purposes, Gapped BLAST can be utilised as described in Altschul et al. (1997) Nucleic Acids Res. 25:3389-3402. Alternatively, PSI-Blast can be used to perform an iterated search which detects distant relationships between molecules (Id.). When utilising BLAST, Gapped BLAST, and PSI-Blast programs, the default parameters of the respective programs (e.g., XBLAST and NBLAST) can be used. Another example of a mathematical algorithm utilised for the comparison of sequences is the algorithm of Myers and Miller, CABIOS (1989). The ALIGN program (version 2.0) which is part of the CGC sequence alignment software package has incorporated such an algorithm. Other algorithms for sequence analysis known in the art include ADVANCE and ADAM as described in Torellis and Robotti (1994) Comput. Appl. Biosci., 10:3-5; and FASTA described in Pearson and Lipman (1988) Proc. Natl. Acad. Sci. 85:2444-8. Within FASTA, ktup is a control option that sets the sensitivity and speed of the search.

Typically, the amino acid sequences of each peptide for use in the invention may have at least 70% identity, using the default parameters of the BLAST computer program (Atschul et al., J. Mol. Biol. 215, 403-410 (1990)) provided by HGMP (Human Genome Mapping Project), at the amino acid level, to the native amino acid sequences. More typically, the amino sequence may have at least 75%, 80%, 85%, 90%, 91%, 92%, 93%, 94%, 95%, 96%, 97%, 98% or at least 99% identity, at the amino acid level to the sequence found in the viral protein. Typically, such amino acids retain the function of the original peptide, i.e. the function of generating T cell responses.

The peptide may therefore be a variant of the respective sequence that is found in a viral protein. As used herein the term "variant" relates to peptides which have a similar amino acid sequence and/or which retain the same function. For instance, the term "variant" encompasses peptides that include one or more amino acid additions, deletions, substitutions or the like. In the present invention, variants of the peptides of the invention retain the function of generating T cell responses.

An example of a variant of the present invention is a peptide that is the same as the native peptide, apart from the substitution of one or more amino acids with one or more other amino acids. The skilled person is aware that various amino acids have similar properties. One or more such amino acids of a peptide or protein can often be substituted by one or more other such amino acids without eliminating a desired activity of that peptide or protein.

Thus the amino acids glycine, alanine, valine, leucine and isoleucine can often be substituted for one another (amino acids having aliphatic side chains). Of these possible substitutions it is preferred that glycine and alanine are used to substitute for one another (since they have relatively short side chains) and that valine, leucine and isoleucine are used to substitute for one another (since they have larger aliphatic side chains which are hydrophobic). Other amino acids which can often be substituted for one another include: phenylalanine, tyrosine and tryptophan (amino acids having aromatic side chains); lysine, arginine and histidine (amino acids having basic side chains); aspartate and glutamate (amino acids having acidic side chains); asparagine and glutamine (amino acids having amide side chains); and cysteine and methionine (amino acids having sulphur containing side chains).

Substitutions of this nature are often referred to as "conservative" or "semi-conservative" amino acid substitutions.

Amino acid deletions or insertions can also be made relative to the native sequence in the viral protein. Thus, for example, amino acids which do not have a substantial effect on the activity of the peptide, or at least which do not eliminate such activity, can be deleted. Such deletions can be advantageous, particularly with longer polypeptides since the overall length and the molecular weight of a polypeptide can be reduced whilst still retaining activity. This can enable the amount of polypeptide required for a particular purpose to be reduced —for example, dosage levels can be reduced.

Amino acid insertions relative to the sequence of the native peptide can also be made. This can be done to alter the properties of a peptide for use in the present invention (e.g. to enhance antigenicity).

Amino acid changes can be made using any suitable technique e.g. by using site-directed mutagenesis or solid state synthesis.

It should be appreciated that amino acid substitutions or insertions within the scope of the present invention can be made using naturally occurring or non-naturally occurring amino acids. Whether or not natural or synthetic amino acids are used, it is preferred that only L-amino acids are present.

Suitably the peptides of the peptide library may be sourced from the same one or two or more viral proteins. The viral proteins may be taken from the same strain of virus. For instance, in the case of influenza A, the peptides of the library may be derived from the matrix (M), nucleoprotein (NP) or polymerase (PB 1 or PB2) proteins. Peptides derived from the matrix (M) or nucleoprotein (NP) are particularly preferred.

In some embodiments, the library of peptides may span the at least one viral protein. In one embodiment the library of peptides may span more than one viral protein, for example two or three viral proteins. In one embodiment the library of peptides may span the entire viral proteome. A proteome is the entire set of proteins expressed by a genome, cell, tissue or organism. Thus the library of peptides may contain a series of peptides that collectively cover a major portion (e.g. greater than 25%, 50%, 75% or 90%) or substantially all (e.g. greater than 99%) of the at least one protein or the entire proteome of the virus, with each peptide having at least the degree of identity to the corresponding native sequence mentioned above. The series of peptides may start with a peptide covering the first few amino acids of the at least one protein or proteome of the virus, and may include peptides which in total cover the major portion or all or substantially all of the at least one protein or proteome of the virus.

The library of peptides in some embodiments may be devised such that they are contiguous; together covering the sequence of at least one protein or the proteome of the virus. In one embodiment, the peptides cover the at least one protein or proteome of the virus sequentially. In other words comparing the sequence of the library of peptides against the viral protein or proteome shows complete single coverage. For example the first peptide covers amino acids 1 to 15, the second peptide covers amino acids 16 to 30, the third amino acid covers amino acids 31 to 45 and so on. In other embodiments the library of peptides may be devised such that each peptide has a sequence overlap with an adjacent peptide. In other words comparing the sequences of the library of peptides against the viral protein or proteome shows each part of the viral sequence is found within more than one peptide. For example the first peptide covers amino acids 1 to 15, the second peptide covers amino acids 10 to 20, the third peptide covers amino acids 15 to 25 and so on. In one embodiment, the peptides are from 16 to 20 amino acids, typically 18 amino acids, long. In one embodiment, the peptides overlap by 8 to 12 amino acids, typically 10 amino acids.

In still further embodiments the library of peptides may be devised such that comparing the peptides against the viral protein or proteome reveals sequence gaps between one peptide and the next.

The peptide and the library of peptides may typically be synthetic peptides. Thus, the peptides for use in the invention may be obtained synthetically, for example by the production of synthetic DNA and expression there from. Methods for the production of synthetic peptides are well known in the art. Peptides can be designed using software, for example the Los Alamos National Library web-based software PeptGen and synthesised using various commercially available platforms, for example using the proprietary PEPscreen technology from Sigma-Aldrich. Peptides can alternatively be produced recombinantly. Peptides for use in the invention are typically in a purified form. Peptides for use in the invention may include one or more non-natural amino acids. Peptides may be conjugated to one or more further moieties, for example polyethylene glycol (PEG) (Veronese F. M. (2001) Biomaterials 22 pp 405-417). Using these techniques, the person skilled in the art would have no difficulty in providing a library of peptides to be screened in accordance with the invention, where each peptide is at least 70% identical (or more as described above) to a respective sequence taken from the same at least one viral protein, and where the peptides in the library optionally span part or all of at least one known viral protein, for instance an influenza A protein.

As described above, the peptide is suitably a member of a library of peptides that are derived from one or more proteins —or the entire proteome —of the virus with which the subject has been inoculated and infected. In this way many peptides derived from the viral proteome may be screened simultaneously to identify the one or ones which induce a T cell response.

The screening methods of the first and second aspect of the invention involve contacting a peptide with a test sample comprising T cells obtained from blood from a subject who has been infected with the virus. This step is typically carried out in vitro or ex vivo. The step of taking a blood sample may not therefore form part of the invention.

The test sample comprising T cells may be a whole blood sample, a fraction of whole blood or typically a sample of peripheral blood mononuclear cells (PBMCs). Such a sample can be obtained, for example, by separating PBMCs from whole blood by density gradient centrifugation. The blood can be heparinised prior to such separation. PBMCs include any blood cell having a round nucleus. Cell types include for example lymphocytes, monocytes or macrophages. These are the blood cells providing a critical component in the immune system to fight infection and adapt to intruders. The lymphocyte population consists of T cells (CD4 and CD8 positive ~75%), B cells and NK cells (~25% combined). The PBMC population also includes basophils and dendritic cells. The test sample comprising T cells comprises CD4+ T cells and CD8+ T cells, in certain embodiments the test sample comprises CD4+ T cells.

The subject from whom the test sample comprising T cells has been obtained has been inoculated and becomes infected with a virus prior to the test sample comprising T cells being taken.

Preferably, the subject from whom the test sample comprising T cells has been obtained has not been vaccinated against the virus. Optionally the subject has not been vaccinated against the virus within the preceding 12 months. More preferably the subject from whom the test sample comprising T cells has been obtained has not been vaccinated against the virus with a vaccine designed to elicit a T cell response. Optionally the subject has not been vaccinated against the virus with a vaccine designed to elicit a T cell response within the preceding 12 months.

When the sample comprising T cells is obtained, the subject is currently infected with the virus or has recently been infected with replicating virus. This can include subjects recently infected with the virus and where symptoms of the infection have subsided. Generally the sample comprising T cells is obtained 0 to 28 days from inoculation and infection with the virus. Therefore a subject currently infected or recently infected with the virus is a subject in whom viral replication has been detected within the past 28 days. Viral replication is detected from a nasal wash or swab with one positive sample by tissue culture or two positive samples by PCR.

The methodologies described herein are advantageous because the exact time of inoculation is known. Test samples may be obtained at known time points after inoculation. A test sample may be obtained at approximately 12, 24, 36 or 48 hours after inoculation. A test sample may be obtained between 1 and 28 days after inoculation such as at 2, 3, 4, 5, 6 or 7 days after inoculation up to 10, 14, 15, 20, 21 or 28 days after inoculation. Multiple test samples may be obtained at differing but known time points after inoculation.

By "inoculated" is meant the placement of something into the human or animal body that will grow or reproduce, typically to produce or boost immunity to a particular disease. The word "inoculation" is sometimes used to mean "vaccination" and therefore the word "inoculated" is also used herein to mean "vaccinated". For example, inoculation may be the non-surgical intra-nasal introduction of inoculum.

The subject from whom the test sample comprising T cells has been obtained typically lacks virus-specific antibody responses, in other words lacks antibodies to the virus with which the subject has been inoculated and has become infected. This can also be described as lacking humoral immunity to the particular virus, or the subject being seronegative for a particular virus. Determination of whether or not a subject has antibodies to a particular virus can be carried out by any suitable means, for example using a hemagglutination assay.

Advantageously the subject is free from other infection. In some embodiments the subject has been free from infection for the preceding 2 weeks or more, such as 1 month or 2 months, or 3 months, or 6 months.

The methodologies described herein are advantageous because each subject is confined to an isolation unit and therefore any contact with pathogens, viruses or bacteria, can be controlled. Conveniently the subject may be in isolation to control and preferably prevent infection with any other infectious agent other than the particular virus. Isolation may commence prior to infection. Isolation may continue until a test sample has been obtained.

The screening methods of the present invention are applicable to all viruses. This is because the scientific community is not aware of any viral infection where T cells do not play a role. T cells function in the human response to a huge and disparate range of viral pathogens. The screening methods of the present invention investigate how the immune system raises a T cell response to a virus and how this affects illness.

The virus with which the subject has been inoculated and become infected in the methods of the present invention may be a virus causing acute self-limiting viral infection. The virus with which the subject has been inoculated and become infected in the methods of the present invention may be a virus which is safe for use in a human viral challenge model. In other embodiments the virus with which the subject has been inoculated may be an attenuated virus or a modified virus, optionally the virus is attenuated or modified so that infection is self-limiting. The virus may be a respiratory virus, an enteric virus, a mucosal virus or a virus that infects by the mucosal route, or a blood borne virus. In embodiments the virus may be a respiratory virus, an enteric virus or a mucosal virus. Optionally the virus may be a respiratory virus.

Viruses which may be of use in the screening methods of the present invention can include:
Orthomyxoviridae (including influenza A, B, C discussed further below),
Paramyxoviridae (including respiratory syncytial virus (RSV), metapneumovirus, measles, mumps and Parainfluenza types 1, 2, 3 and 4),
Coronaviridae,
Picornaviridae (including rhinoviruses and enteroviruses),
Caliciviridae (including noroviruses),
Flaviviridae (including Hepatitis virus C, Dengue virus, Nile West virus) and
Reoviridae (including rotavirus).

The virus with which the subject has become infected may be an enteric virus, such as norovirus.

The virus with which the subject has become infected may be a respiratory virus, such as an influenza virus, rhinovirus (HRV), respiratory syncytial virus (RSV), human metapneumovirus, adenovirus, coronavirus, boca virus, or other acute respiratory virus. In preferred embodiments a respiratory virus may be influenza virus, rhinovirus or respiratory syncytial virus. In one embodiment, the virus is an influenza virus. The influenza virus is typically influenza A. The influenza A may be of subtype H1N1 or H3N2.

Influenza (commonly referred to as the flu) is an infectious disease caused by RNA viruses of the family Orthomyxoviridae (the influenza viruses) that affects birds and mammals. The most common symptoms of the disease are chills, fever, sore throat, muscle pains, severe headache, coughing, weakness/fatigue and general discomfort.

The influenza viruses make up three of the five genera of the family Orthomyxoviridae. Of these, influenza A virus is most common in humans. Influenza B and C also infect humans but are less common. The type A viruses are the most virulent human pathogens amongst the three types of influenza and cause the most severe disease. In the first aspect of the invention, the virus may be influenza A.

The influenza A virus can be subdivided into different serotypes or subtypes based on the antibody response to these viruses. The subtypes that have been confirmed in humans are H1N1, H1N2, H2N2, H3N2, H5N1, H7N2, H7N3, H7N7, H9N2 and H10N7. Of these, H1N1 was responsible for the 1918 influenza pandemic and swine flu in 2009 and H5N1 caused avian flu (or bird flu) in 2004. In the first aspect of the invention, the influenza A may suitably be of subtype H1N1 or H3N2.

The subject is typically a human subject, but the method of the invention also finds use when the subject is a veterinary subject, i.e. an animal.

The subject may have been inoculated and become infected with the virus immediately prior to the test sample being taken. However, the test sample may suitably have been taken some time after inoculation of the subject with the virus, to give the subject's immune system time to react to the virus and for a T cell response to have been raised. For example, the sample may have been taken from the subject from 0 to 28 days after inoculation, or around 1 to 21 days after inoculation of the subject with the virus. Typically, the sample may have been taken from the subject from 2 to 14 days, more typically from 3 to 10 days, more typically from 4 to 8 days, for example 7 days after inoculation of the subject with the virus. Advantageously the sample is taken at a known number of days post inoculation.

The screening methods of the first and second aspect of the invention involve quantifying the T cell response to the peptide in the test sample. This step may be carried out ex vivo or in vitro. By "quantifying the T cell response" is meant quantifying any response of T cells to said peptide. Typically, the T cell response that is quantified may be the production of one or more cytokines, for example IFNγ.

The T cell response, for example the production of one or more cytokines, can be quantified using any suitable means. For example, the response can be quantified using an ELISPOT (enzyme-linked immunosorbent spot) assay. The ELISPOT assay is based on the ELISA immunoassay and allows visualisation of the secretory product of individual activated or responding cells. Each spot that develops in the assay represents a single reactive cell. Thus, the ELISPOT assay provides information both on the type of protein produced by a particular cell and the number of reactive cells. Typically, the ELISPOT assay may be an IFNγ ELISPOT assay. Suitably, the ELISPOT assay may be carried out in 96-well plates. A variety of other methods of quantifying the T cell response will be known to the person skilled in the art.

In one embodiment, the T cell response is quantified. As noted above, T cells can be either CD4+ or CD8+. In another embodiment, the T cell response of both $CD4^+$ and $CD8^+$ T cells may be quantified at the same time, and then a second assay may be carried out to determine what proportion of the T cell response can be attributed to $CD4^+$ T cells. This may be done, for example, by depletion of CD8+ T cells and then carrying out a further ELISPOT assay for the same cytokine, for example an IFNγ ELISPOT assay. This may be useful when studying certain viral infections, for example influenza.

The screening methods of the first aspect of the invention involve comparing the T cell response to the peptide in a test sample from a subject who has been inoculated and infected with the virus to the T cell response to the peptide in a control sample.

The control sample comprising T cells has been obtained from a subject who has not been infected with the virus. Therefore the control sample comprising T cells was obtained from a subject who was not raising a T cell response to the virus. The control sample may have been taken from a subject prior to viral challenge. Such a subject is also referred to herein as a control subject.

The control subject typically also lacks virus-specific antibody responses, in other words lacks antibodies to the virus with which the subject is inoculated. This can also be described as lacking humoral immunity to the particular virus, or the subject being seronegative for a particular virus. Determination of whether or not a subject has antibodies to a particular virus can be carried out by any suitable means, for example using a haemagglutination assay.

In some embodiments the control sample may have been taken from the same subject as the test sample; that is the control sample may have been taken from the subject prior to inoculation and infection with the virus, while the test sample has been taken from the subject after inoculation and infection. Preferably the test sample is obtained at a known number of days post infection. Quantifying the responses of T cells obtained from blood from a subject who has not been inoculated with the virus and is not currently or recently been infected with the virus is typically carried out in vitro or ex vivo. The peptide is contacted with the control sample comprising T cells that have been obtained from the control subject. The step of taking the control blood sample may not form part of the invention. The control sample comprising T cells can be the same type of sample described above in relation to the test sample or can be different. The control sample comprising T cells may be a whole blood sample, a fraction of whole blood or typically a sample of PBMCs. The control sample comprising T cells generally comprises CD4+ T cells and CD8+ T cells, in certain embodiments the control sample comprises CD4+ T cells, for example when studying influenza.

Quantifying the responses of T cells in the control sample to the peptide may be quantified as described above for the test sample.

The method of the first aspect of the invention may also involve the steps of contacting the peptide with the control sample comprising T cells and quantifying the T cell response to said peptide in the control sample comprising T cells prior quantifying contacting the peptide with the test sample comprising T cells and quantifying the T cell response to said peptide in the test sample. Therefore the order of the steps of the screening methods of the present invention may vary.

Thus, in one embodiment, the method of the first aspect of the invention for screening a peptide from a library of peptides for T cell reactivity comprises the following steps:
(a) contacting the peptide with a test sample comprising T cells obtained from a subject that has been infected with a virus;
(b) quantifying the T cell response to the peptide in the test sample comprising T cells;
(c) contacting the peptide with a control sample comprising T cells obtained from a subject that has not been infected with a virus;
(d) quantifying the T cell response to the peptide in the control sample comprising T cells; and
(e) comparing the T cell response in step (b) to the T cell response in step (d);
wherein an increased T cell response in step (b) compared to the T cell response to the peptide in the control sample in step (d) is indicative of the peptide having T cell reactivity.

In the method of the first aspect of the invention, indication that a peptide has T cell reactivity, may mean that peptide is useful in the preparation of a vaccine composition.

In the methods of the invention, optionally test and control samples comprising T cells are obtained from a plurality of subjects i.e. more than one subject. For example, the methods require samples from more than 2, 3, 4, 5, 6, 7, 8, 9, 10, 12, 15 or 20 subjects. Preferably samples from 20 to 30 or more subjects are required. Optionally more than 25, 30, 40 or 50 subjects are required. This is because different subjects will respond differently to the viral derived peptides to be tested due to differing MHC backgrounds and subtypes and the present invention seeks to identify peptides that are useful in inducing a T cell response across a population of subjects. Optionally, subjects can be MHC typed prior to inoculation and infection to ensure a spread of MHC subtypes representative of the subject population.

In embodiments the screening methods of the present invention comprehend obtaining a marker of progression of infection. The marker of progression of infection is a sign, symptom or aspect of the viral infection which is detectable and which can vary from one subject to another. As noted above, the present invention advantageously links how ill a subject feels with the in vitro or ex vivo information obtained from analysing T cell responses to peptides.

The marker of progression of infection may be a score of the severity of symptoms of the viral infection experienced by a subject. Therefore the methods of the invention include scoring of symptoms experienced during infection by the subject who has been inoculated and becomes infected with the virus and from whom the test sample was obtained A score of the severity of the symptoms experienced by a subject can include recording how ill the subject felt or how noticeable the symptoms of the viral infection were.

The severity of the symptoms displayed by the subject in response to infection with the virus may be quantified. Depending on the virus concerned a variety of different objective or quasi-objective methodologies are available to the person skilled in the art for this.

For instance, in the case of influenza one or more of the following symptoms may be scored. The present inventors have developed a symptom scoring methodology similar to the Jackson score (Jackson et al 1958) and have previously published work based on this (DeVincenzo et al., 2010a; DeVincenzo et al., 2010b; Jackson et al., 1958; Jones et al., 2009; Zaas et al., 2009). In summary, twice daily volunteers complete a diary card on which they rate their symptoms on a four point scale from 0 to 3 corresponding to absent to severe.

The symptoms assessed may be one or more nasal stuffiness, runny nose, sore throat, cough, sneezing, ear ache/pressure, breathing difficulty, muscle aches, fatigue, headache, feverish feeling, hoarseness, chest discomfort and overall discomfort. A total symptom score for a day may be obtained by adding the individual symptom scores for a particular day's morning and evening sessions. The individual symptoms may be divided into three subgroups: system symptoms (muscle aches, fatigue, headache and fever), upper respiratory symptoms (nasal stuffiness, ear ache/pressure, runny nose, sore throat and sneezing) and lower respiratory symptoms (cough, breathing difficulty, hoarseness and chest discomfort). Oral temperatures can also be measured daily, for example 2, 3 or 4 times a day. Fever may be considered to be an oral temperature >37.7° C.

For any viral infection a subject or the supervising medical practitioner can score one or more symptoms experienced during the infection.

The one or more symptoms to be assessed and scored depend on the specific viral infection. Optionally two, three, four or five or more different symptoms are scored.

Score cards can be generated for the use of the subjects. A score or recording of the symptoms of the viral infection can be taken at the time the test sample is obtained. A score or recording of the symptoms of the viral infection can be taken every other day, daily, twice a day, three times a day, every 8 hours, every 6 hours, every 4 hours, every 3 hours, every 2 hours, every hour, such as hourly during waking hours following inoculation with the virus.

Scoring can be quasi-objective, objective, or a combination of both. Quasi-objective scoring can be for example with a score on a scale from 0 to 3, or on a scale from 0 to 10 corresponding from absent to severe being used. Scoring can be objective with a recording of one or more of temperature, mucus production volume, lung function, percentage swelling or number of sneezes being used.

It has been found that there is a correlation between reduced severity of symptoms in a subject infected with a virus and induced or pre-existing T cell immunity.

In the present invention reduced symptom scores can mean lower scores, i.e. that a subject feels less ill and/or has fewer or less severe symptoms, than usually attributed to infection with the virus under investigation. In embodiments involving a plurality of subjects reduced symptom scores can mean reduced scores in comparison with another test subject.

The marker of progression of infection can be viral shedding or viral load. Therefore the screening methods of the present invention can include obtaining a measure of viral shedding or viral load. Viral shedding or viral load can be assessed via nasal washes from samples derived via, for example, nasal washes, nasal swabs, nasopharyngeal swabs, bronchial alveolar lavage or other techniques of collecting virus containing samples.

The marker of progression of infection can be duration of illness experienced by a subject. Therefore the screening methods of the present invention can include recording the duration of illness. Duration of illness can be measured from the start of a symptom of the viral infection until cessation of the symptom of the viral infection. For some viruses duration of illness can be measured in days. Alternatively, for other viral infections the duration of illness can be measured in hours.

The marker of progression of infection can be a measure of a biomarker modulated in a subject during infection with a virus. In some embodiments a plurality of biomarkers modulated during infection may be used. The biomarker selected may be one which is typically increased during infection with a virus. Alternatively, the biomarker selected may be one which is typically decreased during infection with a virus.

The screening methods of the present invention can include obtaining a measure of more than one marker of progression of infection. In some embodiments, both symptom scores and viral shedding information may be used. In some embodiments, symptom scoring and illness duration may be selected. In other embodiments, viral shedding and illness duration may be assessed. In further embodiments symptom scoring, viral shedding and illness duration may provide useful information.

It may be regarded that a peptide to which the subject's T cells respond in the screening methods of the first aspect of the present invention, is a viral peptide (or a peptide with a suitably similar sequence) "seen" by the subject's immune system during infection and to which an immune response was raised. It follows that, if the subject experienced a milder infection, as determined by reduced symptom scores, then memory T cells responding to that peptide confer T cell immunity and are valuable in protection against disease. In other words a peptide of the invention provokes a T cell response, preferably a CD4+ T cell response, with a magnitude that correlates inversely with the severity of symptoms associated with a viral infection.

The screening methods of the present invention may require a step of identifying a correlation between a marker of progression of infection and T cell responses, optionally the magnitude of the T cell responses. The correlation may be performed using one or more of the methodologies available to investigate a relationship between two variables.

In embodiments in which the marker of progression of infection is symptom scores, the screening methods can identify a correlation between lower symptom scores and the magnitude of the T cell responses. The screening methods can include identifying an inverse correlation between symptom scores and T cell responses. This can identify a peptide able to ameliorate infection.

In embodiments in which the marker of progression of infection is duration of illness, the screening methods can identify a correlation between shorter duration of illness and the magnitude of the T cell responses. The screening methods can include identifying an inverse correlation between illness duration and T cell responses. This can identify a peptide able to ameliorate infection.

In embodiments in which the marker of progression of infection is viral shedding, the screening methods can identify a correlation between lower viral shedding and the magnitude of the T cell responses. The screening methods can include identifying an inverse correlation between viral shedding and T cell responses. This can identify a peptide able to ameliorate infection.

In embodiments in which the marker of progression of infection is a biomarker typically increased during infection with a virus, the screening methods can identify a correlation between biomarker levels and the magnitude of the T cell responses. The screening methods can include identifying an inverse correlation between biomarker level and T cell responses. This can identify a peptide able to ameliorate infection.

In embodiments in which the marker of progression of infection is a biomarker typically decreased during infection with a virus, the screening methods can identify a correlation between biomarker levels and the magnitude of the T cell responses. The screening methods can include identifying a positive correlation between biomarker level and T cell responses. This can identify a peptide able to ameliorate infection.

The screening methods of the second aspect of the present invention involve contacting a peptide with a test sample comprising T cells obtained from blood from a subject who is subsequently infected with the virus. The step is typically carried out in vitro or ex vivo. The step of taking a blood sample may not therefore form part of the invention.

The test sample comprising T cells may be described as above. In the screening methods of the second aspect of the invention the test sample may be referred to as a T0 test sample.

In the screening methods of the second aspect of the present invention, the subject from whom the test sample comprising T cells has been obtained has not yet been inoculated or become infected with a virus.

The subject from whom the test sample comprising T cells has been obtained is typically seronegative for a particular virus. Determination of whether or not a subject has antibodies to a particular virus can be carried out by any suitable means, for example using a haemagglutination assay.

The virus of interest in the second aspect of the present invention is as described above with respect to the first aspect of the present invention.

The subject is typically a human subject, but the method of the invention also finds use when the subject is a veterinary subject, i.e. a non-human animal.

As described above the peptide is suitably a member of a library of peptides that are derived from one or more proteins—or the entire proteome of the virus. In this way many peptides derived from the viral proteome may be screened simultaneously to identify the one or ones which induce a T cell response.

The screening methods of the second aspect of the invention involve quantifying the T cell response to the peptide in the test sample. The step may be carried out as described above.

The screening methods of the second aspect of the present invention may involve the subject from whom the test sample comprising T cells is obtained subsequently being inoculated and becoming infected with the virus. It follows that if the subject experiences a milder infection as determined by a marker of progression of infection such as reduced symptom scores, as described above, then this may be the result of memory T cells. Peptides identified as inducing T cell responses in samples comprising T cells obtained from subjects who subsequently experience a milder infection, may be peptides capable of conferring T cell immunity and being valuable in protection against disease.

In the methods of the second aspect of the invention, indication that a peptide induces a response may mean that peptide is useful in the preparation of a vaccine composition.

In the methods of the invention, optionally test samples comprising T cells are obtained from more than one subject. For example, the method requires samples from more than 5, 6, 7, 8, 9, 10, 12, 15 or 20 subjects. Preferably samples from 20 to 30 more subjects are required. This is for the reasons described above.

In another embodiment the screening method further comprises the step of testing the effectiveness of the identified peptide in inducing T cell immunity to the particular virus. In this step a subject seronegative for the particular virus is vaccinated with the identified peptide. Thereafter the subject is infected with the particular virus and symptoms of the infection are scored and compared against symptom scores of a subject seronegative for the particular virus who was not vaccinated with the identified peptide prior to infection with the particular virus.

In the methods disclosed herein, inoculation of a subject with a virus is via intra-nasal introduction of a virus.

The methods of the first and second aspect of the invention have been used to identify peptides according to the third aspect of the invention that are derived from a strain of influenza A virus and provoke a $CD4^+$ T cell response in a sample comprising T cells from a subject who was seronegative for that strain of the virus. As disclosed below, the magnitude of the $CD4^+$ T cell response was found to correlate inversely to the severity of symptoms suffered by a subject who was initially seronegative for a strain of virus when inoculated with that strain of the virus. Therefore detection and quantification of CD4+ T cell responses are preferred.

The screening methods of the first and second aspect of the present invention identify a peptide capable of inducing a T cell response and inducing T cell immunity and/or ameliorating a viral infection. The methods can further include steps which determine whether the identified peptide is cross-reactive and is therefore also valuable in inducing a T cell response and inducing T cell immunity and/or ameliorating a viral infection against more than one virus or more than one strain or subtype of a virus. For example a peptide can be capable of inducing a T cell response and inducing T cell immunity and/or ameliorating a viral infection to more than one strain or subtype of influenza.

The screening methods of the first and second aspects of the present invention can further include a step of testing whether T cells which respond to the identified peptide can also respond to an equivalent peptide from a second virus or a second strain or subtype of the virus. If T cells can demonstrate a capability to cross-recognise an equivalent peptide from a second virus or a second strain or subtype of the same virus, both peptides are valuable as they can be used to induce T cell responses to both strains or subtypes of the virus. In other words the peptides are cross-reactive. Either peptide can be used to vaccinate against both viruses or both viral strains or subtypes.

The screening methods of the first and second aspects of the present invention may therefore include a step of contacting T cells which responded to a peptide identified in the screening methods with an equivalent peptide having a level of identity with the equivalent region of the equivalent protein of a second virus and quantifying the response of the T cells to the equivalent peptide, wherein an above background response is indicative of cross-recognising T cells and therefore indicative of the identified peptide and the equivalent peptide being cross-reactive.

An equivalent peptide generally refers to a peptide of similar sequence to the identified peptide. The differences in sequence between the identified peptide and the equivalent peptide may derive from the differences in protein sequence between different strains or subtypes of a virus. Preferably, an equivalent protein refers to the protein having the same designation. For example, the NP protein of a first influenza A strain or subtype can be the equivalent protein to the NP protein from a second influenza A strain or subtype. As an alternative example, the M protein of a first influenza A strain or subtype can be the equivalent protein to the M protein from a second influenza A strain or subtype. A level of identify is as described above.

It is expected that the methods of the first and second aspect of the invention may be used to screen for peptides according to the third aspect of the invention that are derived from viruses other than influenza and give rise to a similar T cell response in patients infected with such a virus. This is because T cell responses are mounted by the immune system to all viruses. Therefore, since T cells are an integral part of the immune response, T cell responses are a valuable part of the immune system's defences against any virus and the methods of the present invention are applicable to identifying peptides expected to induce T cell immunity to any viral infection.

A third aspect of the present invention provides a peptide that is at least 70% identical to a sequence found within the proteome of a virus and which provokes a T cell response.

The peptide is therefore predicted to be capable of inducing T cell immunity to a virus. The third aspect of the present invention encompasses peptides obtainable by the screening method of the first and second aspect of the present invention described above.

The present inventors used a human challenge model of influenza infection, as described in the Example below, to identify certain peptides which induce a T cell response The T cell response is preferably a CD4+ T cell response. Therefore the peptides are predicted to be capable of inducing T cells immunity.

The sequences of the peptides identified by the inventors are shown in Table 1 below together with their SEQ ID NOs. The peptides having the sequences of SEQ ID NOs: 6-12, 14-15 and 18-20 were identified from an H3N2 subtype of influenza A and the peptides having the sequences of SEQ ID NOs: 23-26 and 29-31 were identified from an H1N1 subtype of influenza A.

TABLE 1

| Amino acid sequence | SEQ ID NO | SEQ ID NO as in sequence listing |
|---|---|---|
| LKREITFHGAKEIALSY | 6 | 1 |
| HRSHRQMVATTNPLIKH | 7 | 2 |
| IKHENRMVLASTTAKAM | 8 | 3 |
| EIRASVGKMIDGIGRFYI | 9 | 4 |
| KLSDHEGRLIQNSLTIEK | 10 | 5 |
| PIYRRVDGKWMRELVLY | 11 | 6 |
| GKWMRELVLYDKEEIRRI | 12 | 7 |
| SNLNDATYQRTRALVR | 14 | 8 |
| TYQRTRALVRTGMDPRM | 15 | 9 |
| KFQTAAQRAMVDQVRESR | 18 | 10 |
| GQTSVQPTFSVQRNLPF | 19 | 11 |
| TFSVQRNLPFEKSTIMAA | 20 | 12 |
| VKLYRKLKREITFHGAKE | 23 | 13 |
| RMVLSAFDERRNKYLEEH | 26 | 14 |
| GENGRKTRIAYERMCNIL | 26 | 15 |
| IAYERMCNILKGKFQTAA | 30 | 16 |
| QPTFSVQRNLPFDKTTIM | 31 | 17 |

The present invention also encompasses peptides comprising sequences at least 70% identical to a sequence listed above, optionally the peptide may be at least 80% or 90% or 95% identical to a sequence listed above. The present invention also encompasses fragments of such peptide sequences of lengths as described above. Additionally the present invention provides peptides consisting of the sequences identified in Table 1.

In Table 1 above, and throughout this specification, the amino acid residues are designated by the usual IUPAC single letter nomenclature. The single letter designations may be correlated with the classical three letter designations of amino acid residues as follows:

A = Ala
C = Cys
D = Asp
E = Glu
F = Phe
G = Gly
H = His
I = Ile
K = Lys
L = Leu
M = Met
N = Asn
P = Pro
Q = Gln
R = Arg
S = Ser
T = Thr
V = Val
W = Trp
Y = Tyr

The full names of the amino acids are as follows: alanine (A or Ala), cysteine (C or Cys), aspartic acid (D or Asp), glutamic acid (E or Glu), phenylalanine (F or Phe), glycine (G or Gly), histidine (H or His), isoleucine (I or Ile), lysine (K or Lys), leucine (L or Leu), methionine (M or Met), asparagine (N or Asn), proline (P or Pro), glutamine (Q or Gin), arginine (R or Arg), serine (S or Ser), Threonine (T or Thr), tryptophan (W or Trp), tyrosine (Y or Tyr) and valine (V or Val), Where a residue may be aspartic acid or asparagine, the symbols Asx or B may be used. Where a residue may be glutamic acid or glutamine, the symbols Glx or Z may be used. References to aspartic acid include aspartate, and references to glutamic acid include glutamate, unless the context specifies otherwise. The symbol X may be used to denote any amino acid.

Preferred variants of the peptides for use in the present invention include one or more conservative substitutions as defined herein.

A fourth aspect of the present invention is a vaccine comprising one or more peptides capable of inducing a T cell response. The peptides are capable of inducing T cell immunity to a virus. Such peptides may therefore be useful in the preparation of a vaccine composition for the prevention of influenza infection. Such vaccine compositions may be effective in the prophylaxis of influenza infection. The peptides of use in a vaccine are obtainable by the screening method of the first aspect of the present invention and may include the peptides of the second aspect of the invention.

In other embodiments the vaccine can comprise one or more, two or more, optionally three or more peptides having SEQ ID NO 6, 7, 8, 9, 10, 11, 12, 14, 15, 18, 19, 20, 23, 26, 29, 30 or 31 (corresponding to SEQ ID Nos 1, 2, 3, 4, 5, 6, 7, 8, 9, 10, 11, 12, 13, 14, 15, 16 or 17 in the sequence listing), or peptides at least 70% identical thereto or a fragment thereof.

The vaccine composition of the invention can be formulated for use by any convenient route. The vaccine composition of the invention may be a pharmaceutical composition. The vaccine composition of the invention can alternatively simply be referred to as a composition. The vaccine composition of the invention may suitably include a pharmaceutically acceptable carrier, excipient, diluent, adjuvant, vehicle, buffer or stabiliser in addition to one or more peptides of the invention as the therapeutically or prophylactically active ingredient. Such carriers include, but are not limited to, saline, buffered saline, dextrose, liposomes, water, glycerol, polyethylene glycol, ethanol and combinations thereof.

The vaccine composition may be in any suitable form depending upon the desired method of administering it to a patient.

The vaccine composition can be adapted for administration by any appropriate route, for example by the parenteral (including subcutaneous, intramuscular, intravenous or intradermal or by injection into the cerebrospinal fluid), oral (including buccal or sublingual), nasal, topical (including buccal, sublingual or transdermal), vaginal or rectal route. Such a composition can be prepared by any method known in the art of pharmacy, for example by admixing the peptides with the carrier(s) or excipient(s) under sterile conditions. Typically, the vaccine composition is adapted for administration by the subcutaneous, intramuscular, intravenous or intradermal route, typically by injection. Alternatively, the vaccine composition may be adapted for oral or nasal administration.

A pharmaceutical composition adapted for parenteral administration may be an aqueous and non-aqueous sterile injection solution which can contain anti-oxidants, buffers, bacteriostats and solutes which render the formulation substantially isotonic with the blood of the intended recipient; and aqueous and non-aqueous sterile suspensions which can include suspending agents and thickening agents. Excipients which can be used for injectable solutions include water, alcohols, polyols, glycerine and vegetable oils, for example. The composition can be presented in unit-dose or multi-dose containers, for example sealed ampoules and vials, and can be stored in a freeze-dried (lyophilized) condition requiring only the addition of the sterile liquid carried, for example water for injections, immediately prior to use. Extemporaneous injection solutions and suspensions can be prepared from sterile powders, granules and tablets.

A pharmaceutical composition adapted for oral administration can be presented as discrete units such as capsules or tablets; as powders or granules; as solutions, syrups or suspensions (in aqueous or non-aqueous liquids; or as edible foams or whips; or as emulsions)

Suitable excipients for tablets or hard gelatine capsules include lactose, maize starch or derivatives thereof, stearic acid or salts thereof. Suitable excipients for use with soft gelatine capsules include for example vegetable oils, waxes, fats, semi-solid, or liquid polyols etc.

For the preparation of solutions and syrups, excipients which can be used include for example water, polyols and sugars. For the preparation of suspensions, oils (e.g. vegetable oils) can be used to provide oil-in-water or water in oil suspensions.

A pharmaceutical composition adapted for nasal administration wherein the carrier is a solid include a coarse powder having a particle size for example in the range 20 to 500 microns which is administered in the manner in which snuff is taken, i.e. by rapid inhalation through the nasal passage from a container of the powder held close up to the nose. A suitable composition wherein the carrier is a liquid, for administration as a nasal spray or as nasal drops, may comprise an aqueous or oil solution of the active ingredient.

Pharmaceutical compositions adapted for administration by inhalation include fine particle dusts or mists that can be generated by means of various types of metered dose pressurised aerosols, nebulizers or insufflators.

A pharmaceutical composition adapted for transdermal administration may be presented as a discrete patch intended to remain in intimate contact with the epidermis of the recipient for a prolonged period of time. For example, the active ingredient can be delivered from the patch by iontophoresis as generally described in Pharmaceutical Research, 3(6):318 (1986).

A pharmaceutical composition adapted for topical administration may be formulated as an ointment, cream, suspension, lotion, powder, solution, paste, gel, spray, aerosol or oil. For infections of the eye or other external tissues, for example mouth and skin, the composition may be applied as a topical ointment or cream. When formulated in an ointment, the active ingredient can be employed with either a paraffinic or a water-miscible ointment base. Alternatively, the active ingredient can be formulated in a cream with an oil-in-water cream base or a water-in-oil base. A pharmaceutical composition adapted for topical administration to the eye may comprise eye drops wherein the active ingredient is dissolved or suspended in a suitable carrier, especially an aqueous solvent. A pharmaceutical composition adapted for topical administration in the mouth may comprise lozenges, pastilles or mouth washes.

The pharmaceutical composition may contain preserving agents, solubilising agents, stabilising agents, wetting agents, emulsifiers, sweeteners, colourants, odourants, salts (substances of the present invention can themselves be provided in the form of a pharmaceutically acceptable salt), buffers, coating agents or antioxidants.

The vaccine composition of the invention may also contain one or more other prophylactically or therapeutically active agents in addition to the at least one peptide as defined herein.

The peptide for use in the vaccine compositions of the invention may or may not be lyophilised.

The vaccine composition of the invention may also include a pharmaceutically acceptable adjuvant in addition to the peptide(s) as defined herein. Adjuvants are added in order to enhance the immunogenicity of the vaccine composition.

Suitable adjuvants for inclusion in a vaccine composition are known in the art and include incomplete Freund's adjuvant, complete Freund's adjuvant, Freund's adjuvant with MDP (muramyldipeptide), alum (aluminium hydroxide), alum plus *Bordatella pertussis* and immune stimulatory complexes (ISCOMs, typically a matrix of Quil A containing viral proteins).

The vaccine composition of the invention may also include or be co-administered with one or more co-stimulatory molecules, such as B7, and/or cytokines, such as an interferon or an interleukin, that can promote T cell immune response such as Il-2, IL-15, IL-6, GM-CSF, IFNγ or other cytokines promoting T cell responses. This can be done in addition to conventional adjuvant, as described above.

Dosages of the vaccine composition of the present invention can vary between wide limits, depending upon the age and condition of the individual to be treated, etc. and a physician will ultimately determine appropriate dosages to be used.

This dosage can be repeated as often as appropriate. For example, an initial dose of the vaccine may be administered and then a booster administered at a later date.

For administration to mammals, and particularly humans, it is expected that the daily dosage of the active agent will be from 1 μg/kg to 10 mg/kg body weight, typically around 10 μg/kg to 1 mg/kg body weight. The physician in any event will determine the actual dosage which will be most suitable for an individual which will be dependent on factors including the age, weight, sex and response of the individual. The above dosages are exemplary of the average case. There can, of course, be instances where higher or lower dosages are merited, and such are within the scope of this invention.

The vaccine composition of the invention can be administered by any convenient route as described herein, such as via the intramuscular, intravenous, intraperitoneal or oral routes or by injection into the cerebrospinal fluid.

The vaccine composition of the invention can be administered to patients felt to be in greatest need thereof, for example to children or the elderly. Timing of administration of the vaccine may be important; for example a vaccination strategy can be put in place once an outbreak of influenza has been identified, in order to prevent the spread of the virus in a community. The vaccine composition can be used in particular subsets of patients, for example those who have not already suffered from a particular strain of influenza, for example seasonal flu.

The method of prophylaxis can be of a human or non-human animal subject and the invention extends equally to uses in both human and/or veterinary medicine. The vaccine of the invention is suitably administered to an individual in a "prophylactically effective amount", this being sufficient to show benefit to the individual.

The vaccine composition of the invention can be provided in unit dosage form, will generally be provided in a sealed container and may be provided as part of a kit. Such a kit would normally (although not necessarily) include instructions for use. It can include a plurality of said unit dosage forms.

Accordingly, in yet another aspect, the present invention provides a kit of parts comprising a vaccine composition of the invention and one or more cytokines and/or adjuvants in sealed containers.

In yet another aspect, the present invention provides a kit of parts comprising a vaccine composition of the invention and one or more cytokines and/or adjuvants for separate, subsequent or simultaneous administration to a subject.

Preferred features for the second and third and subsequent aspects of the invention are as for the first aspect mutatis mutandis.

A fifth aspect of the present invention is a peptide capable of inducing T cell immunity for use in a method of treatment or prophylaxis of influenza. Alternatively, the fifth aspect of the present invention is the use of a peptide capable of inducing T cell immunity for the manufacture of a medicament for the treatment or prophylaxis of influenza.

The peptide of can be a peptide obtainable by the first or second aspect of the present invention. In other embodiments the peptide can be a peptide of the second aspect of the present invention. The peptide can be a peptide having SEQ ID NO 6, 7, 8, 9, 10, 11, 12, 14, 15, 18, 19, 20, 23, 26, 29, 30 or 31, (corresponding to SEQ ID Nos 1, 2, 3, 4, 5, 6, 7, 8, 9, 10, 11, 12, 13, 14, 15, 16 or 17 in the sequence listing), or a peptide at least 70% identical thereto or a fragment thereof.

A fifth aspect of the present invention also provides a method for the treatment or prophylaxis of influenza comprising administering to an individual in need thereof a peptide capable of inducing T cell immunity. Optionally the peptide is obtainable by the first or second aspect of the present invention. Alternatively, the peptide can be a peptide having SEQ ID NO 6, 7, 8, 9, 10, 11, 12, 14, 15, 18, 19, 20, 23, 26, 29, 30 or 31, (corresponding to SEQ ID Nos 1, 2, 3, 4, 5, 6, 7, 8, 9, 10, 11, 12, 13, 14, 15, 16 or 17 in the sequence listing), or a peptide at least 70% identical thereto or a fragment thereof.

Following is a description by way of example only with reference to the accompanying drawings of embodiments of the invention. In the drawings:

BRIEF DESCRIPTION OF THE DRAWINGS

FIG. 1 shows an Elispot layout of experimental influenza A infection in humans. (a) H3N2 challenge study (A/Wisconsin/67/05) T cell Elispot layout. (b) H1N1 challenge study (A/Brisbane/59/07) T cell Elispot layout. Freshly isolated 300,000 PBMC were put into each well and stimulated with peptide pool at 2 µg/ml for 18-24 hours.

IDENTIFICATION OF PEPTIDES FOR FLU VACCINE AS VALIDATION OF SCREENING METHODS

Figure 2:
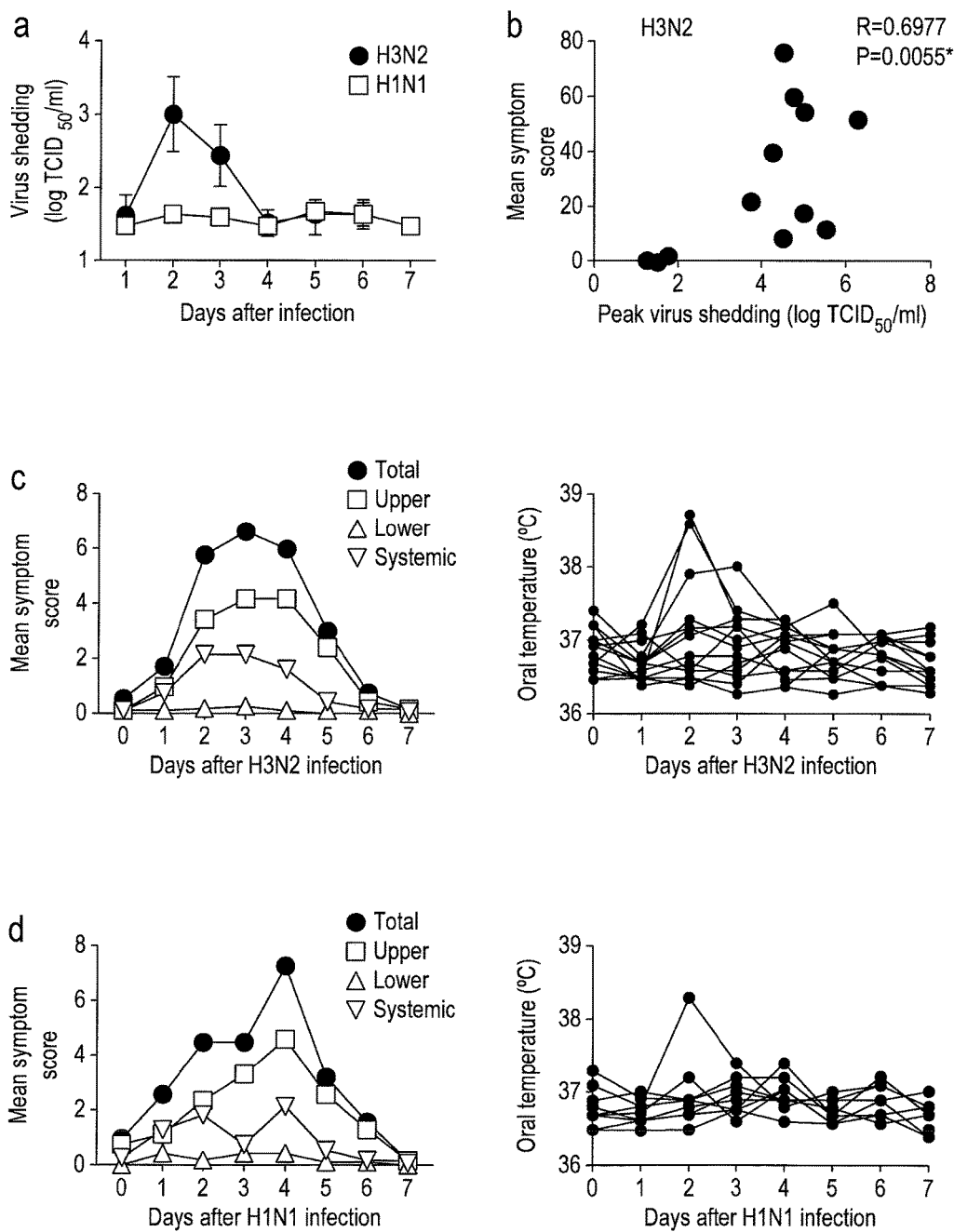
FIG. 2 shows viral shedding in nasal wash, seroconversion and symptom development in seronegative healthy volunteers experimentally infected with influenza A. (a) Volunteers infected with cell grown H3N2 (WS/67/05) virus or egg-grown H1N1 (BR/59/07) virus. The virus in the nasal sample was titrated by $TCID_{50}$ assay. Presence of flu-specific antibody was measured by haemagglutination inhibition assay. (b) Correlation of total symptom scores against the peak nasal virus shedding in H3N2 infected subject by Spearman rank correlation test. (c) Mean symptom scores and oral temperatures of volunteers infected with H3N2 virus. (d) Mean symptom scores and oral temperatures of volunteers infected with H1N1 virus. Symptom assessments were performed by the volunteers twice daily on a four-point scale (absent to severe). The score for each symptom group was obtained by adding the total individual symptom scores for that particular group on that particular day. Oral temperatures were determined four times a day for the duration of the study and the highest temperature was represented.

This study was designed to allow several effects to be demonstrated, including the following points.

Firstly, the study confirmed that pre-existing cell mediated immunity to a virus (in other words the existence of memory T cells within a subject, which respond to peptide antigens of a virus) results in a reduction in disease symptoms, duration of disease and viral shedding, when the subject is infected with that virus.

Secondly, the cognate peptide antigens for the pre-existing memory T cells were identified. These peptides can be used to induce T cell immunity to the virus.

Thirdly, the study demonstrates the effectiveness of the screening method of the invention for identifying peptides which correspond to antigens inducing T cell responses during immune response to viral infection. These peptides can be used to induce T cell immunity in a virus.

Materials and Methods

Study Design

Between October, 2008 and October, 2009, two separate prospective, randomised, and double blinded, parallel group clinical studies of experimental human influenza A infections were undertaken in a single site in Cambridge, UK. The two studies were carried out 9 months apart. An H3N2 challenge study was carried out between 24 Oct. and 24 Nov., 2008 whereas H1N challenge study was carried out between 18 Aug. and 18 Sep., 2009. Healthy, non-pregnant adults between the ages 18 and 45 were eligible for the enrolment. Exclusion criteria included health care workers, history of acute respiratory illness, chronic illness or medications. In H3N2 challenge study, a total of 17 healthy adult volunteers, which are haemagglutination-inhibition (HI) titres less than 1:8 to influenza A/Wisconsin/67/05, were enrolled in the study. Whereas, in H1N1 challenge study, a total of 24 healthy adult volunteers with HI titres less than 1:8 to influenza A/Brisbane/59/07 were enrolled in the study.

Both studies were conducted in compliance with Good Clinical Practice guidelines (CPMP/ICH/135/95) and declaration of Helsinki. The protocols were approved by East London and City and the Southampton and Southwest Hampshire ethics review committees. Written informed consent was obtained from each participant with an ethics committee approved form. No medications, except acetaminophen for treatment of severe symptoms, were permitted. Subjects were compensated for their participation of the study.

Study Outline

Screening assessments began within 45 days of the scheduled viral inoculation. Volunteers were confined to individual rooms in an isolation unit 2 days before the day of inoculation, and remained in isolation for 7 days thereafter. Therefore, contact with any pathogens such as viruses or bacteria is completely controlled. Isolation and monitoring of subjects allows study of infection and symptoms of the infection. Inoculation occurs under clinical conditions so that the exact time of inoculation is known. Therefore samples obtained from the subject can be taken at known time points after inoculation.

The subjects were randomised into 4 groups and each group of the participants were inoculated intra-nasally with different doses of influenza A virus on day 0. The dose of the virus was designated as 1:10 (high), 1:100 (medium-high), 1:1000 (medium-low) and 1:10,000 (low) from the original virus stock. Group 1 received high dose, Group 2 received medium-high dose, Group 3 received medium-low and Group 4 received low dose of virus. Nasopharyngeal swab were collected daily from baseline day 0 during the quarantine period for virus isolation. Serum samples were taken daily for serum cytokine and biomarker study. Fresh whole blood for cellular assays was taken on day −2 or 0, 7 and day 28. An additional time point day 3 was taken for H1N1 study.

Oral temperatures were measured four times daily. Fever was defined as an oral temperature >37.7° C. Symptom assessments were performed by the volunteers twice daily on a four-point scale (0-3 corresponding to absent to severe)

(Hayden et al., J. Clin. Invest. 101(3), 643-649, 1998). The symptoms assessed were nasal stuffiness, runny nose, sore throat, cough, sneezing, earache/pressure, breathing difficulty, muscle aches, fatigue, headache, feverish feeling, hoarseness, chest discomfort, and overall discomfort. The total symptom score for each day was obtained by adding the individual symptoms scores for that particular day including morning and evening sessions. The individual symptoms contributing to the total symptoms scores were divided into three subgroups: systemic symptoms (muscle aches, fatigue, headache, and fever), upper respiratory symptoms (nasal stiffness, ear ache/pressure. runny nose, sore throat, and sneezing) and lower respiratory symptoms (cough, breathing difficulty, hoarseness and chest discomfort).

Viruses

In both challenge studies, GMP grade viruses were manufactured and processed by GlaxoSmithKline, UK. The stock virus were diluted to four different inoculum titres and prepared in individual aliquots intended for single use and then administered. The titre of the stock virus was $10^7$ $TCID_{50}$ infectious dose. They were ten-fold diluted and the titre were ranged from high titre (1:10), medium-high (1:100), medium-low titre (1:1,000) and low titre (1:10,000). Subjects were observed for potential allergic reactions for 30 min following inoculation. In H3N2 challenge study, tissue culture grown A/Wisconsin/67/05 virus was used. In H1N1 challenge study, egg grown A/Brisbane/59/2007 virus was used.

Virus Titration by $TCID_{50}$ (Tissue Culture Infectious Dose 50%) Assay

Viral load in the nasopharyngeal samples were determined by TCID.sub.50 assay as described by the WHO manual of Animal Influenza: Serial ten-fold dilutions of virus-containing samples were inoculated into 96-well microtitre plates seeded with Madin-Darby canine kidney (MDCK) cells, and incubated for 5-6 days at 37.degree. C. Cytopathic effects in individual wells were determined via light microscopy. Titre greater than 1:5 was considered positive.

Hemagglutination Inhibition (HI) Assay

Hemagglutinin-specific antibody titers against H1N1 (A/Brisbane/59/2007) or H3N2 (A/Wisconsin/67/05) in the serum samples were determined by HI assay using chicken erythrocytes as described in WHO manual Synthetic Peptides 18-mer peptides overlapping by 10 amino acid residues and spanning the full proteome of the H1N1 and H3N2 influenza A viruses were designed using the Los Alamos National Library web-based software PeptGen and synthesized (purity >70%; PEPscreen; Sigma-Aldrich) using the sequences of the following strains: A/Brisbane/59/2004 (H1N1), A/New York 388/2005 (H3N2) (surface proteins), and A/New York 232/2004 (H3N2) (internal proteins). In H3N2 peptides, the amino acid sequence homology between challenge Wisconsin strain and New York strain was greater than 99%. The total numbers of peptides used in detecting antigen-specific responses for H1N1 and H3N2 were 554 and 601 respectively.

Identifying Peptides "Seen" by T Cells of Immune System

Figure 1:
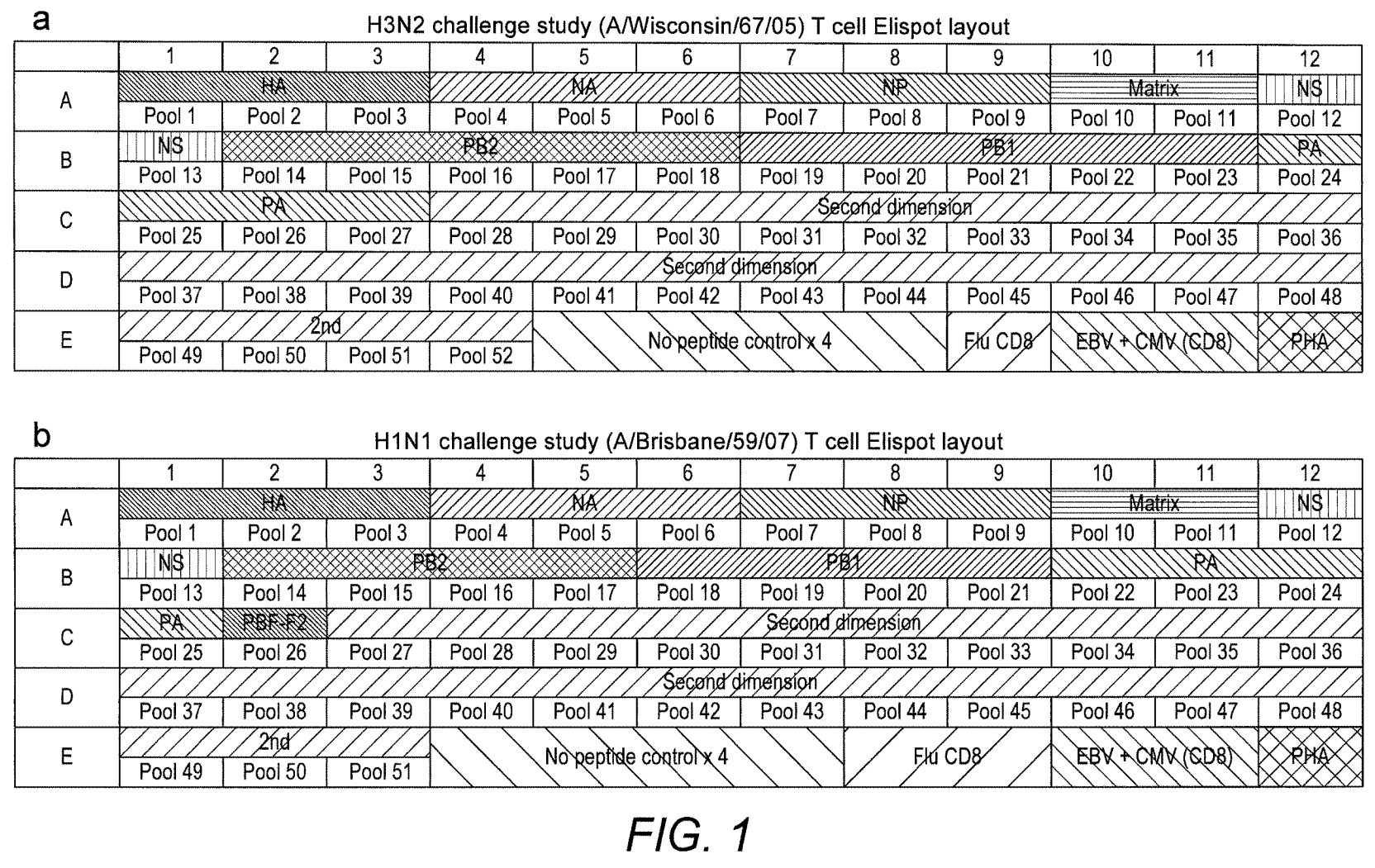

Ex vivo IFNγ ELISPOT assays were used to identity T cells which respond to stimulation with a specific peptide and therefore secrete IFNγ. In the each influenza Elispot assay, all overlapping peptides in each individual were simultaneously tested using 2-dimensional matrices with a total of 50 pools ($1^{st}$ D=25 pools; $2^{nd}$ D=25 pools; up to 25 peptides/pool) so that each peptide was present in two different pools (see FIG. 1 for Elispot layout). Peptides were used at a final concentration of 2 μg/ml each. The putative peptide from each positive response well could be deconvoluted from a 2-dimensional matrix system where each peptide only appeared once in each dimension. The putative peptides were then confirmed individually in the second Elispot assay with the same input cell number per well.

Ex Vivo IFN-γ ELISPOT Assay

Peripheral mononuclear cells (PBMC) were separated from 50 ml heparinised blood by density gradient centrifugation using Lymphoprep (Axis-Shield, Norway) and Leucosep tube (Greiner, UK) within 3-6 hour upon each bleed (Li et al., J. Immunol. 181, 5490-5500 2008). To detect influenza-specific effector memory cells (CD45RO+), PBMC were added into 96-well Elispot Multiscreen plates (MAIPS4510, Millipore) at 300,000 cells/well and cultured with peptide pools for 18-24 h incubation at 37° C. and 5% $CO_2$. The end concentration of each peptide in each well was 2 μg/ml, for both peptide pools and individual peptides. All ELISPOT assays were performed using the human IFN-γ ELISPOT kit (Mabtech) according to the manufacturer's instructions. The internal negative control was no peptide in quadriplicates, and positive controls were EC (a mixture of EBV and CMV T cell epitope peptides) or PHA (10 μg/ml). The spots on each well were counted using an automated ELISPOT reader and AID ELISPOT 3.1.1 HR software (Autoimmune Diagnostika). In pool responses, wells containing spot numbers greater than the mean+4 SD of three negative control wells (no peptide) were regarded as positives in each individual, provided that the total was greater than 50 spot forming cells (SFC)/million PBMC, to rule out false positives where background was very low. In all assays, values of no peptide control wells were 1.8±4.6 SFC/million PBMC for 150 healthy subjects and 2±5.7 SFC/million PBMC for 150 influenza-exposed subjects. Values of T cell responses were all background subtracted and presented in SFC/million PBMC. To determine whether T cells were CD4 or CD8, in the second ELISPOT assay, cell depletion was also conducted by Dynal CD8 beads, as described in the manufacturer's instructions (Invitrogen, UK), before the ELISPOT assay. Undepleted PBMC served as positive controls. For single peptide confirmation Elispot assay, response greater than 10 SFC/million PBMC was considered positive after background substraction and when T cell lines could be generated from respective peptides and tested positive again with ICS.

Generation of Short-Term T Cell Lines

Short-term T cell lines were generated to confirm influenza peptides and the CD4 or $CD8^+$ property of each peptide by ICS and flow cytometry, as described previously (Li et al., J. Immunol. 181, 5490-5500, 2008). In brief, frozen samples of PBMC were thawed and rested for 2 h before stimulating with 10 μg/ml of each peptide at final concentration for 1 h. Cells were cultured in RPMI 1640 supplemented with 10% human serum (National Blood Services, UK) and 25 ng/ml IL-7 (PeproTech) for 3 days, and then 100 U of IL-2/ml (Proleukin, Novartis UK) was added every 3 to 4 days thereafter. On day 14, cells were washed three times with sterile PBS and then rested in fresh RAB-10 for 25 to 35 h at 37° C., 5% $CO_2$.

FACS Staining Assay

Activated (CD38+) and proliferating (Ki67+) cells in freshly isolated PBMC were stained by were stained with mAbs against human Ki67-FITC (Clone B56, BD Biosciences), DR-PE (clone TU36, BD) CD38-APC (clone HB7, BD), CD4-pacific blue (Clone MT130, DakoCytomation), and CD8-PE-Cy5 (Clone SK1, BD). Cytotoxicity as measured by expression CD107a (clone H4A3, BD) and IFN-γ

(clone XMG1. 2, BD) in both CD4 and CD8 memory cells were also studied ex vivo using frozen PBMC as described previously (Li et al., J. Immunol. 181, 5490-5500 2008). PBMC (1 million per stimulation) were stimulated with peptide pools for 6 hours in the presence of brefeldin A and monensin. For each stimulation condition, at least 500,000 total events were acquired using LSRII (BD immunocytometry Systems, San Jose, Calif.). Data analysis was performed using FlowJo (version 8.8.4; TreeStar, Ashland, Oreg.). Response greater than 3 times background was considered positive.

Chromium Release Assay

A standard $^{51}$Cr release assay was used as described previously (McMichael A J et al., N Engl J Med 309, 13-17, 1983). T cell lines generated from PBMC samples were used as effector cells and their autologous EBV-transformed B cell lines were used as target cells. Inhibition of perforin-mediated cytotoxicity was obtained by incubating the CD4+ T cells for 2 h with 100 nM concanamycin (Sigma). Specific $^{51}$Cr release was calculated from the following equation: ([experimental release-spontaneous release]/[maximum release-spontaneous release])×100%.

Statistics

All graphs were presented by GraphPad Prism (version 5) and statistical analysis was done by GraphPad Prism and SPSS. Magnitude of T cells response was presented by SFC/million PBMCV and breadth of T cell response was defined by the number of proteins recognized by each subject. To study the role of T cell in the virus shedding (viral control) and symptom development (immunopathology), correlation was run between pre-existing T cells and measures of infection and illness (virus titre, symptom assessments, temperature) by Spearman rank correlation analysis. Correlation analysis was based on data collected from all infected (culture positive and/or four fold or greater rise in HI antibody titre) individuals.

Epithelial Cell MHC Class II Expression

Immunohistochemistry

Lung explants were harvested from lung tissue recovered from patients undergoing routine thoracic surgery under additional consent. Human parenchymal and bronchial tissue was fixed in acetone prior to embedding in GMA resin. Two millimetre sections were cut sequentially and immunostained using isotype control monoclonal antibodies or antibodies specific for MHC II (HLA-DR) at the same concentration. Signal was amplified using the ABC system, and colour developed using DAB stain. Specific staining is shown in brown, haematoxylin counterstain is shown in blue.

Flow Cytometry

Primary bronchial epithelial cells (PBECs) were obtained from subjects undergoing research bronchoscopies in the Wellcome Trust Clinical Research Facility at Southampton General Hospital. Bronchial brushings were cultured in Bronchial Epithelium Growth Media (BEGM), (Lonza, Wokingham, UK) in collagen coated flasks (PureCol™, Inamed Biomaterials, California, USA) and incubated in a humidified atmosphere at 37° C., 5% $CO_2$. The collection and use of these samples was approved by the Southampton and South West Hampshire Research Ethics Committee (REC No: 06/Q1701/98 & 08/H0504/138).

Influenza A virus strain X31 was supplied at a concentration of 4×10$^7$ pfu/ml (a kind gift of 3VBiosciences). Inactivated virus (UVX31) was prepared by exposure to an ultra-violet (UV) light source for 2 h.

PBECs were seeded at 1×10$^5$ cells per well onto a collagen-coated 24 well plate and left at 37° C., 5% $CO_2$ for 24 h. Cells were then growth media starved for 24 h in 0.5 ml Bronchial Epithelium Basal Media (BEBM) supplemented with 1 mg/ml BSA, insulin, transferrin and selenium (BEBM+ITS). Cells were incubated for 2 h with no virus, or 2×10$^3$ pfu of X31 or UVX31. Cells were then washed three times with BEBM+ITS and incubated for a further 20 h at 37° C., 5% $CO_2$ in 0.5 ml of BEBM-ITS. Cells were dispersed by trypsinisation and prepared for flow cytometric analysis as previously described.

Samples were incubated on ice in the dark for 30 min with Allophycocyanin-Cyanine 7 (APC-Cy7)-conjugated anti-HLA-DR (BD Biosciences, Oxford, UK) or appropriate isotype control (IgG2a BD Biosciences Oxford, UK). After washing, intracellular staining for viral nucleoprotein (NP)-1, was performed using BD Cytofix/Cytoperm kit according to manufacturer's instructions, and AlexFluor 488 (AF488)-conjugated anti-NP-1 antibody (HB-65, a kind gift of 3VBiosciences). Flow cytometric analysis was performed on a FACSAria using FACSDiva software v5.0.3 (all BD).

Results

Human Influenza Infection Model

In order to study the impact of existing cell mediated immunity (CMI) on influenza infection, an experimental infection model was established using live influenza A virus in human volunteers (Oxford J S et al Expert Rev Anti Infect Ther. 3, 1-2 (2005)). A total of 41 healthy volunteers aged between 19 and 41 were inoculated intra-nasally with serial 10 fold dilution of influenza A viruses; a cell grown H3N2 WS/67/05 and an egg grown H1N1 BR/59/07. Subjects were studied prospectively from inoculation in a clinical isolation facility with measures of viral shedding, symptom development, cellular and humoral immune responses for the first 7 days and again at day 28. These measures provide information on the severity of the infection, duration of infection and on the immune responses of the subject to the infection. In the H3N2 challenge study, 8 out of 17 (47%) volunteers were female and the median age was 26.5 yr (range 22-41) (Table 2). In H1N1 challenge study, 7 out of 24 (29%) were female and the median age was 24 yr (range 19-35).

TABLE 2

| | Demography, virus shedding and antibody titre of the study groups | | | | | | | |
|---|---|---|---|---|---|---|---|---|
| | H3N2 challenge group | | | | H1N1 challenge group | | | |
| | Group 1 | Group 2 | Group 3 | Group 4 | Group 1 | Group 2 | Group 3 | Group 4 |
| N | 4 | 4 | 4 | 5 | 6 | 6 | 6 | 6 |
| Age-yr | | | | | | | | |
| Mean ± SD | 26 ± 3 | 28 ± 5 | 25 ± 2 | 29 ± 8 | 25 ± 5 | 25 ± 5 | 27 ± 4 | 23 ± 3 |
| Median | 26 | 27 | 25 | 28 | 24 | 24 | 26 | 22 |
| Range | 23-29 | 25-35 | 22-27 | 22-41 | 20-32 | 22-35 | 23-31 | 19-27 |

TABLE 2-continued

Demography, virus shedding and antibody titre of the study groups

| | H3N2 challenge group | | | | H1N1 challenge group | | | |
|---|---|---|---|---|---|---|---|---|
| | Group 1 | Group 2 | Group 3 | Group 4 | Group 1 | Group 2 | Group 3 | Group 4 |
| Sex-no. (%) | | | | | | | | |
| Female | 2(50) | 2(50) | 2(50) | 2(40) | 2(33) | 1(17) | 2(33) | 2(33) |
| Male | 2(50) | 2(50) | 2(50) | 3(60) | 4(67) | 5(83) | 4(67) | 4(67) |
| Virus shedding no. (%) | 1(25) | 4(100) | 2(50) | 2(40) | 1(17) | 3(50) | 1(17) | 1(17) |
| HAI titre on Day 28 | | | | | | | | |
| Positive | 3(75) | 2(50)* | 1(25)** | 1(25) | 2(33) | 2(33) | 2(33) | 1(17) |
| GMT | 96 | 33 | 0.6 | 0 | 1 | 5 | 0 | 0 |
| Mean symptom scores | | | | | | | | |
| Mean ± SD | 10.5 ± 19.7 | 60.8 ± 10.7 | 13.8 ± 14 | 4.6 ± 5.5 | 11.2 ± 17.7 | 39 ± 23.2 | 14.5 ± 14.1 | 8.3 ± 15.2 |
| Median | 1 | 57.5 | 7.7 | 1 | 11.5 | 44.5 | 14.5 | 0.5 |
| Range | 0-40 | 52-76 | 5-22 | 0-9 | 0-22 | 3-65 | 0-31 | 0-38 |

*One subject was unavailable for D28 visit.
**Two subjects were unavailable for D28 visit.

All volunteers selected were seronegative to the challenge strain and virus PCR negative in nasal lavage at the time of challenge. This confirmed that subjects were not currently infected with the challenge virus, or been infected recently with the challenge virus. The overall infection rate was defined by evidence of virus shedding and/or seroconversion by day 28. This was higher in subjects (14/17, 82%) challenged with H3N2 virus than subjects (9/24, 38%) challenged with H1N1 virus.

In the H3N2 challenge group, virus shedding persisted in individuals for as long as 7 days but most subjects (8/14, 57%) cleared the virus completely by day 4. (FIG. 2a). The H1N1 challenge group, did not exhibit reliable viral shedding —a recognised phenomenon with this egg grown virus (Steel J, et al. J Virol. 2009 February; 83(4):1742-53).

In the H3N2 challenge infection, total symptoms closely tracked peak viral load (FIG. 2b, r=0.6977, p=0.0055, Spearman coefficient). Similar symptom profiles were observed between the two challenge cohorts and were comparable to wild type infections in this population (Newton D W at al. Am J Manag Care. 6, 265-75 (2000)). In the H3N2 challenge group, 11 out of 14 (79%) infected subjects developed one or more symptoms, and as a group, exhibited symptom scores that peaked on day 3 and returned to normal by day 7 after viral inoculation (FIG. 2c). 3 out of 14 subjects (21%) developed fever (oral temperature>37.7° C.) and the highest temperatures were detected on day 2. In the H1N1 group, 8 out of 9 (89%) infected subjects developed one or more symptoms and showed mean symptom scores that peaked on day 4 and returned to normal by day 7 after viral inoculation (FIG. 2d). Also, 1 out of 9 infected subjects (11%) developed fever and the highest temperatures were detected on day 2.

Figure 3:
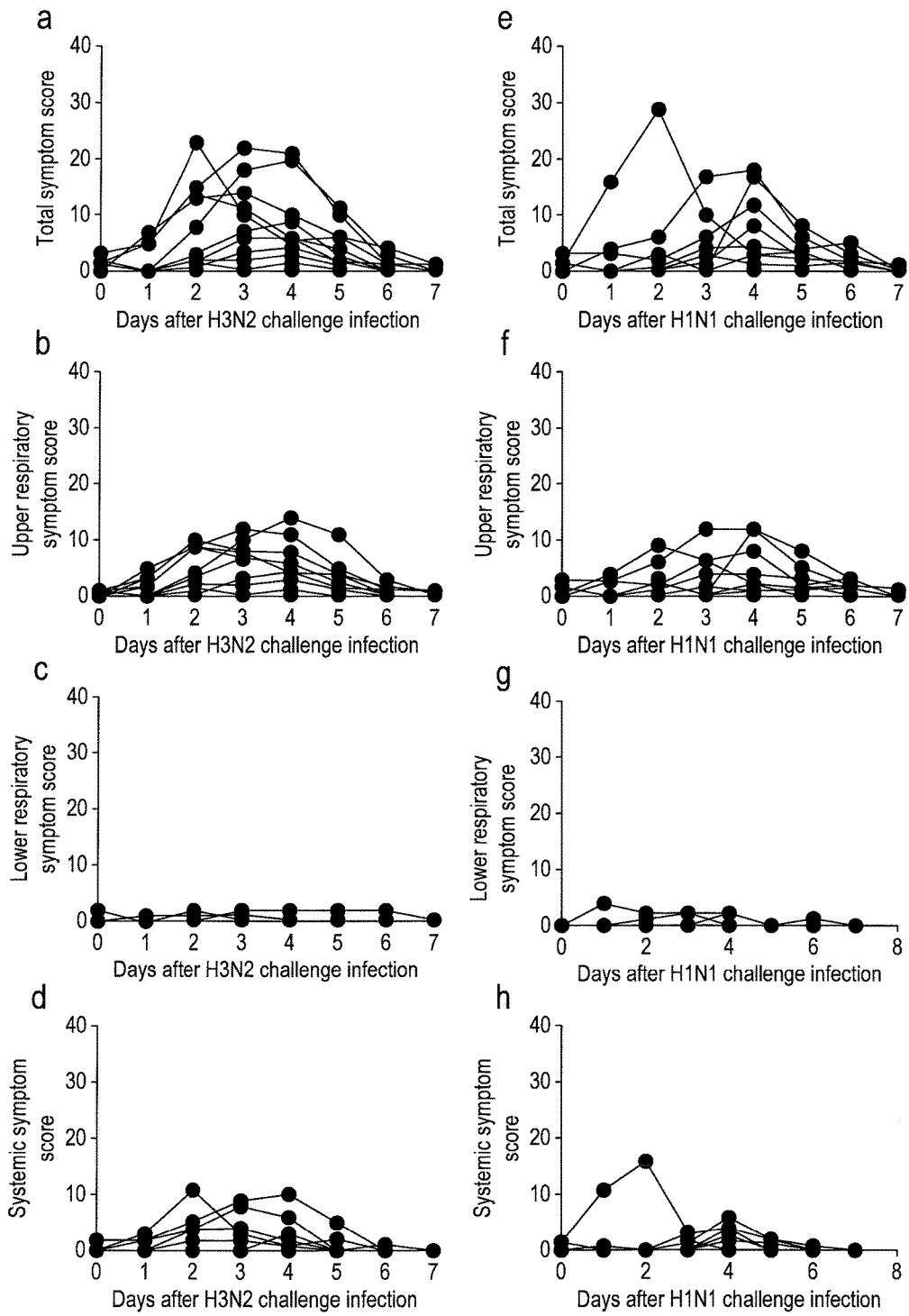
FIG. 3 shows symptom scores in each infected volunteer infected with influenza A.
(a) Total symptom scores (y axis) in volunteers infected with H3N2 (WS/67/05) (x axis showing days after H3N2 challenge infection).
(b) Upper respiratory symptom scores (y axis) in volunteers infected with H3N2 (WS/67/05) (x axis showing days after H3N2 challenge infection).
(c) Lower respiratory symptom scores (y axis) in volunteers infected with H3N2 (WS/67/05) (x axis showing days after H3N2 challenge infection).
(d) Systemic symptom scores (y axis) in volunteers infected with H3N2 (WS/67/05) (x axis showing days after H3N2 challenge infection).
(e) Total symptom scores (y axis) in volunteers infected with H1N1 (BR/59/07) virus (x axis showing days after HiN1 challenge infection).
(f) Upper respiratory symptom scores (y axis) in volunteers infected with H1N1 (BR/59/07) virus (x axis showing days after H1N1 challenge infection).
(g) Lower respiratory symptom scores (y axis) in volunteers infected with H1N1 (BR/59/07) virus (x axis showing days after H1N1 challenge infection).
(h) Systemic symptom scores (y axis) in volunteers infected with H1N1 (BR/59/07) virus (x axis showing days after H1N1 challenge infection).

In both challenge groups, the total symptoms were dominated by upper respiratory illness as defined by the presence of symptoms such as runny nose and sore throat, occurred in 10/14 (71%) subjects in H3N2 group and 8/9 (89%) subjects in H1N1 group. Lower respiratory symptoms such as cough and hoarseness were much milder in severity and occurred in 3/14 (21%) in H3N2 group and 2/9 (22%) in H1N1 group. Scores for systemic symptoms such as muscle aches and fatigue were also present in 6/14 (43%) in H3N2 group and 5/9 (56%) in H1N1 group. For more details on the distribution of symptoms of each infected subject, see FIG. 3.

Antibody and T Cell Responses of Infected Volunteers

All volunteers enrolled were screened to ensure they were sero-negative for antibodies to the challenge virus. However, the antibody responses (HAI titre) were detectable after 7 days post challenge (FIG. 5a), at which time the viruses were completely cleared as indicated in FIG. 2a.

Figure 4:
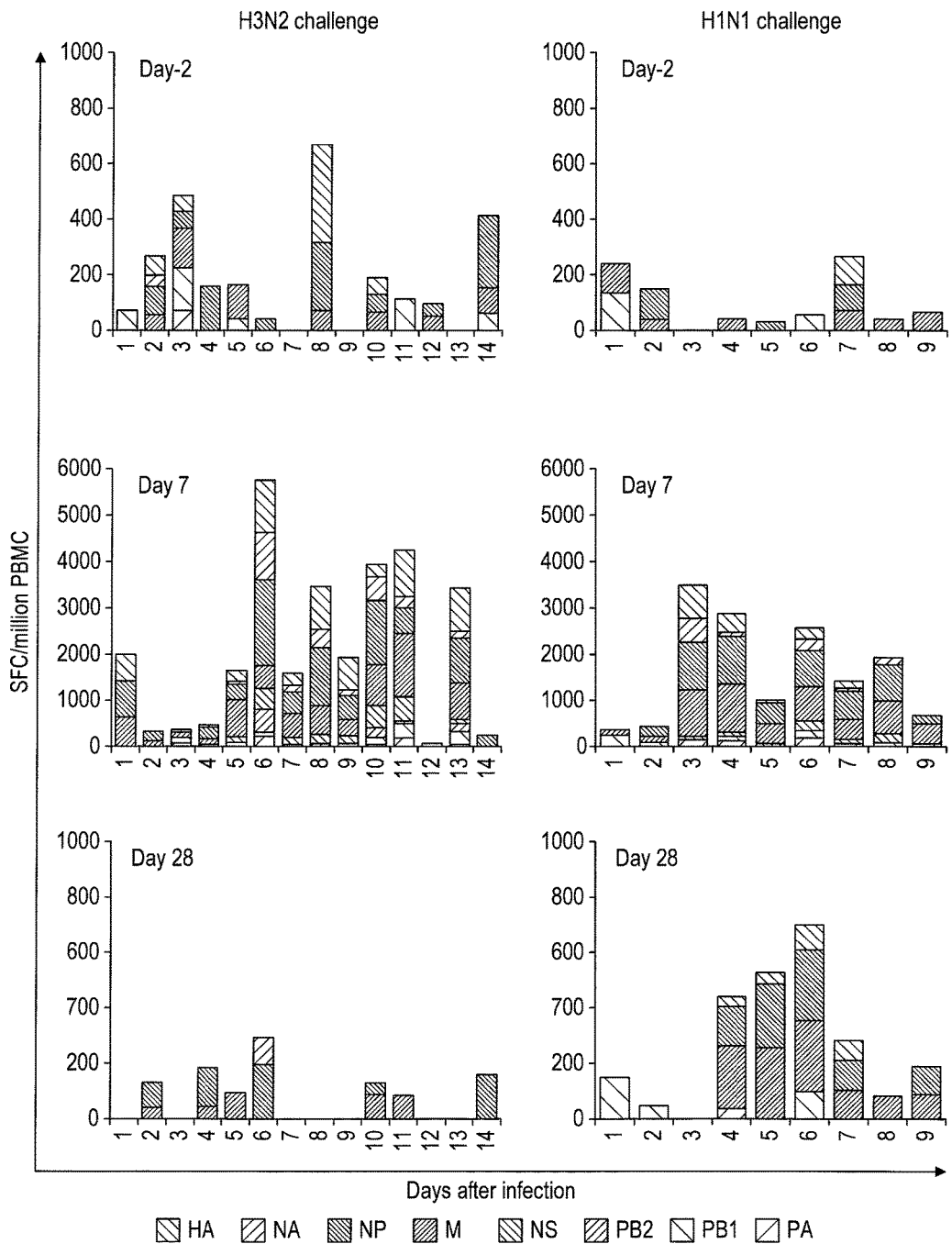
FIG. 4 shows T cell responses in seronegative healthy volunteers experimentally infected with influenza A virus. Flu-specific T lymphocyte responses were measured from freshly isolated PBMC ex vivo from each volunteer by IFN-γ release after stimulation with corresponding peptide pools spanning the entire challenge influenza proteome. Each bar represented the total T cell responses to entire influenza proteome and each colour box represented the response to each protein. X axes denote subject number.

Prior to viral challenge the nature of pre-existing T cell memory from previous infection exposure was determined. T cell responses to proteins expressed by the challenge virus were present in most volunteers in both studies prior to challenge despite the absence of detectable antibodies to the same strains. The size of total T cell responses was below 1000 SFC/million PBMC in all subjects studied at baseline (FIG. 4). At baseline, in the H3N2 group, 11 out of 14 (79%) infected subjects showed memory T cell responses recognizing one or more H3N2 proteins, with an average of two proteins recognized (range 1-5). The most immunodominant proteins were nucleoprotein (8/14, 57%) and matrix proteins (7/14, 50%), which are highly conserved across strains, based on the number of subjects and the magnitude of IFN-γ response. In the H1N1 challenge group, 8 out of 9 (89%) infected subjects showed memory T cell responses that recognized one or more proteins at the baseline, with an average number of one protein recognized (range 1-3). The most immunodominant protein was matrix protein (6/9, 67%). These results show that conserved viral peptide sequences from nucleoprotein and the matrix proteins are important in cell mediated immunity and T cell responses, and the present methods allow identification of these peptides.

On day 7 after challenge infection, both the breadth and magnitude of memory T cell responses increased dramatically in the peripheral blood by an average of 10 fold in both study groups (FIG. 4). In the H3N2 group, 14 out of 14 (100%) of infected subjects demonstrated positive T cell responses with an average of five proteins recognized (range 1-8). Pre-existing T cell responses against each protein were expanded in addition to new responses that had not been detected at baseline. In the H1N1 challenge group, 9 out of 9 (100%) infected subjects were T cell positive responding to an average of five proteins (range 2-7). No significant changes in the T cell responses against known CD8 epitopes of CMV and EBV were found in control wells, suggesting bystander activation was minimal (data not shown). Therefore the body dramatically responds to viral peptides during infection raising T cell responses and the present methods allow identification of those peptides.

On day 28, the total memory T cell response had returned to baseline levels (<1000 SFC/million PBMC) in both challenge groups. Immunodominant protein responses such as NP and M persisted at a baseline level whereas most newly generated responses against other proteins had vanished after the acute phase of infection. In the H3N2 challenge group, 7 out of 14 infected subjects (50%) were T cell positive, with the average number of proteins recognized reduced to 1 (range 1-2). In the H1N1 challenge group, 8 out of 9 infected subjects (89%) were T cell positive, with the average number of proteins recognized reduced to 2 (range 2-4). However, 4 out of 9 (44%) newly generated HA responses persisted at lower levels (average 60 SFC/million PBMC). In addition, epitope mapping and whether they were mediated by CD4 or CD8 T cells was determined for responses to the immunodominant proteins (NP and M) on all baseline samples from both challenge groups. T cell response against immunodominant proteins were predominantly CD4 T cell mediated in both groups (CD4 vs CD8 56% vs 44% for H3N2, and 71% vs 28% for H1N1) (FIG. 5b), consistent with a previous report (Lee L Y et al J Clin Invest. 118, 3478-3490 (2008)).

Figure 5:
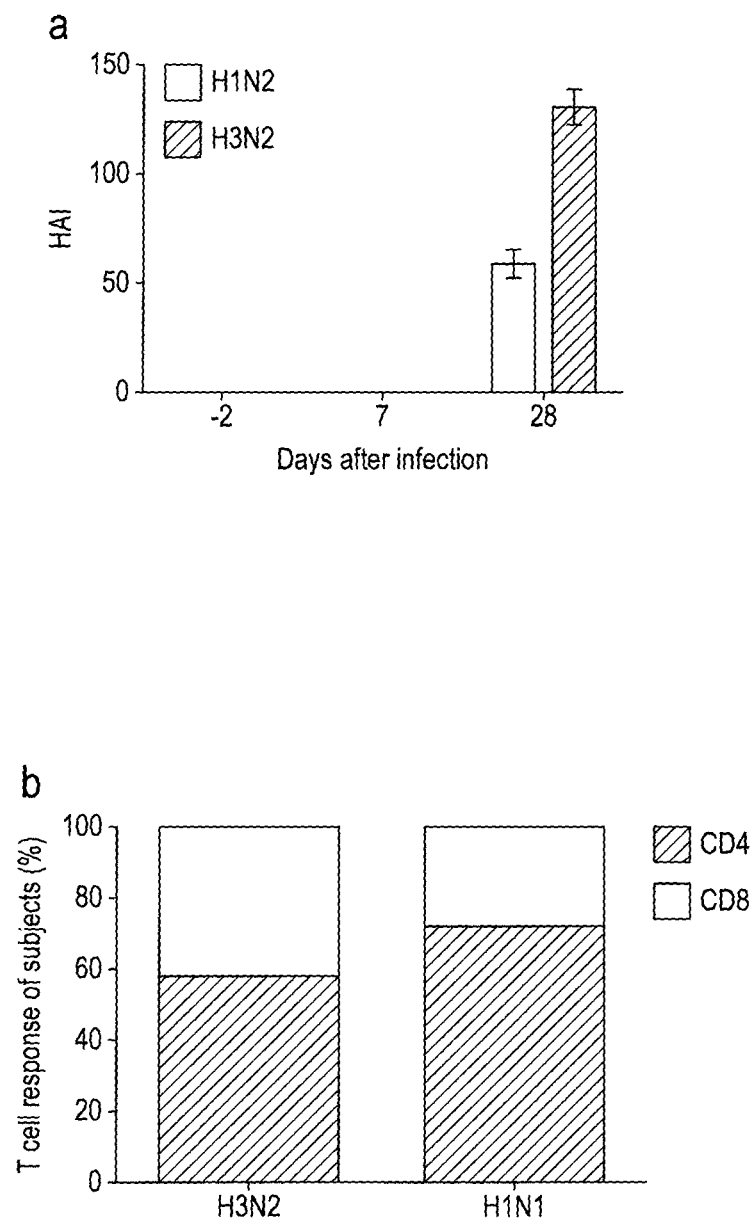
FIG. 5 shows antibody and T cell responses in seronegative healthy volunteers experimentally infected with influenza A virus. (a) Presence of flu-specific antibody was measured by haemagglutination inhibition assay. (b) Plot of proportion of infected subjects demonstrating positive T cell responses to NP and M flu proteins at baseline. The Y-axis represents the proportion (%) of subjects from both challenge studies with positive response to NP and M proteins and their CD4 and CD8 dependency. (c) Activated and proliferating cells (CD38+Ki67+) could be detected ex vivo in H1N1-infected subjects by flow cytometry (d) Changes in the proportion of activated and proliferating (CD38+Ki67+) T cells in both CD4 and CD8 population of freshly isolated PBMC from volunteers infected with H1N1 virus by flow cytometry. (e) Correlation between proportion of CD38$^+$ Ki67$^+$ T cells on day 7 of H1N1 infected subjects with their magnitude of Elispot response by Spearman rank correlation test.
Figure 5:
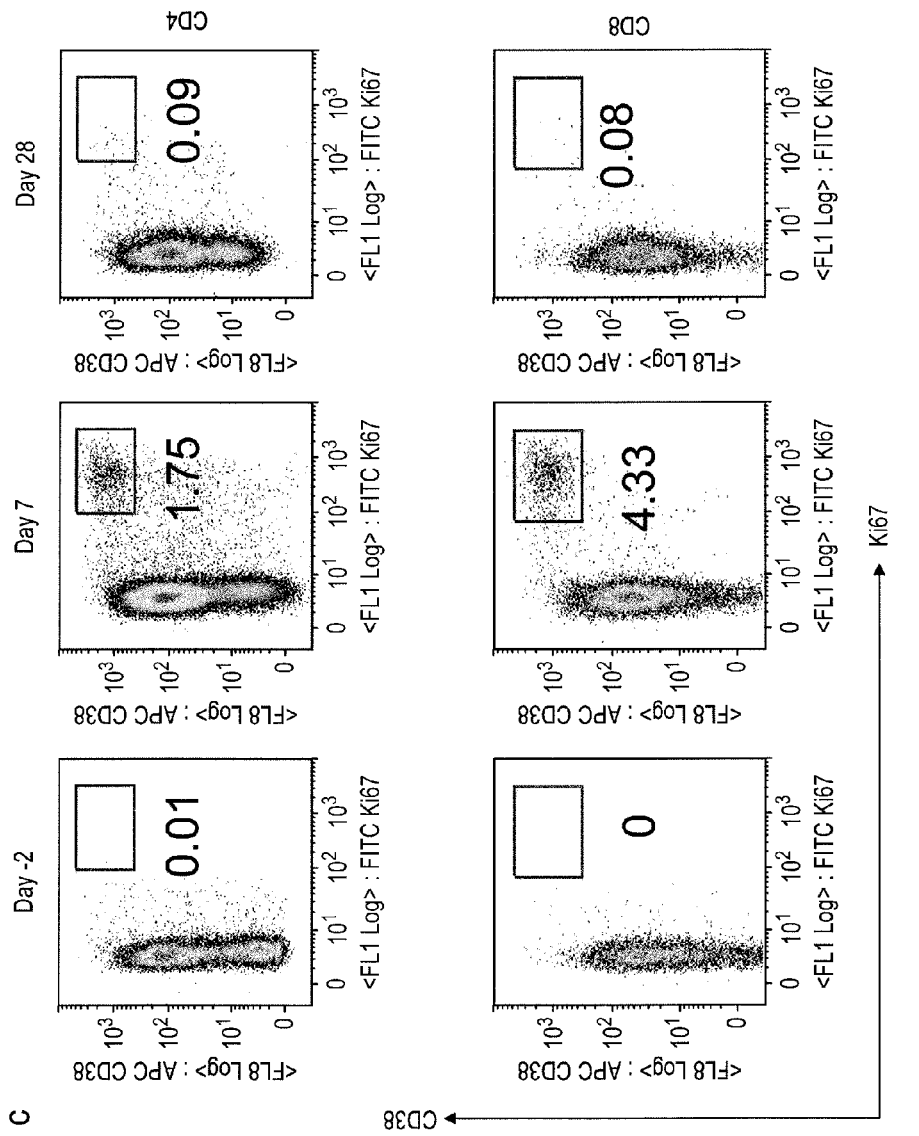
Figure 5:
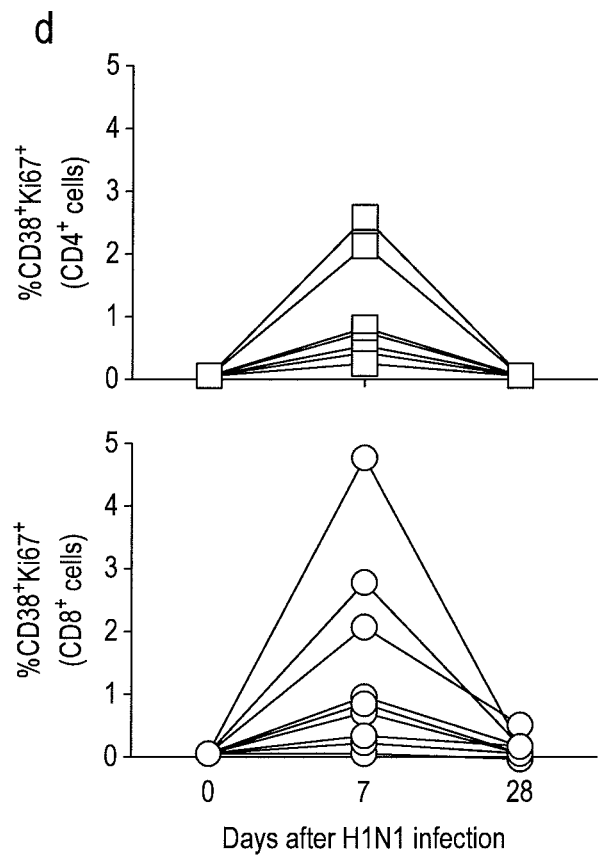
Figure 5:
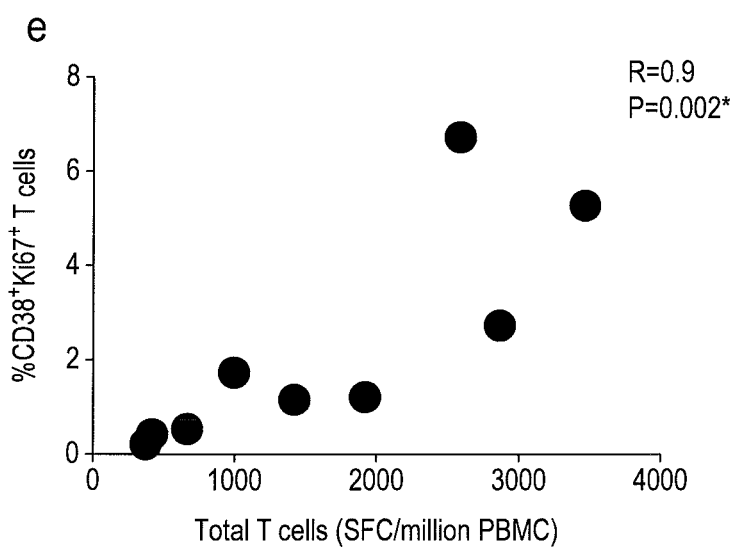

To understand better the kinetics of T cell responses the functional status of both CD4 and CD8 cells during the course of infection with H1N1 virus was studied. Activated (CD38$^+$) and proliferating cells (Ki67$^+$) of both CD4 and CD8 cells from freshly isolated PBMC were undetectable before the challenge (FIG. 5c). Both markers were present on the greatly expanded T cell population on day 7 before returning to baseline level on day 28. (FIG. 5d). The number of Ki67$^+$CD38$^+$ T cells correlated with the frequency of SFC by Elispot on day 7 (FIG. 5e, r=0.9, p=0.002, Spearman coefficient).

Impact of Pre-Existing T Cell Responses on Viral Shedding and Symptom Scores in Experimental Influenza Infection The role of T cells in controlling virus shedding (viral control) (Li I W et al. Chest. 137, 759-68 (2010)) and symptom development (immunopathology) (La Gruta N L et al. Immunol Cell Biol. 85, 85-92 (2007)) was studied. The relationship between pre-existing T cells responding to total and immunodominant influenza proteins (NP+M), virus shedding, total symptom scores and illness duration was analysed. A correlation test (Spearman rank correlation test, Prism 5) was run to see if the magnitude of flu-specific CD4 or CD8 cells were correlative in virus shedding and disease severity as indicated by total symptom scores and length of illness duration in both H3N2 and H1N1 challenge studies. The results clearly showed that the magnitude of CD4 response against immunodominant nucleoprotein (NP) and matrix (M) proteins was inversely correlative to peak virus shedding, symptom scores and illness durations (Table 2). This demonstrates that pre-existing T cell immunity to a virus can ameliorate subsequent infection with that virus. This also shows that the present methods allow determination of the peptides which induce a response.

Figure 6:
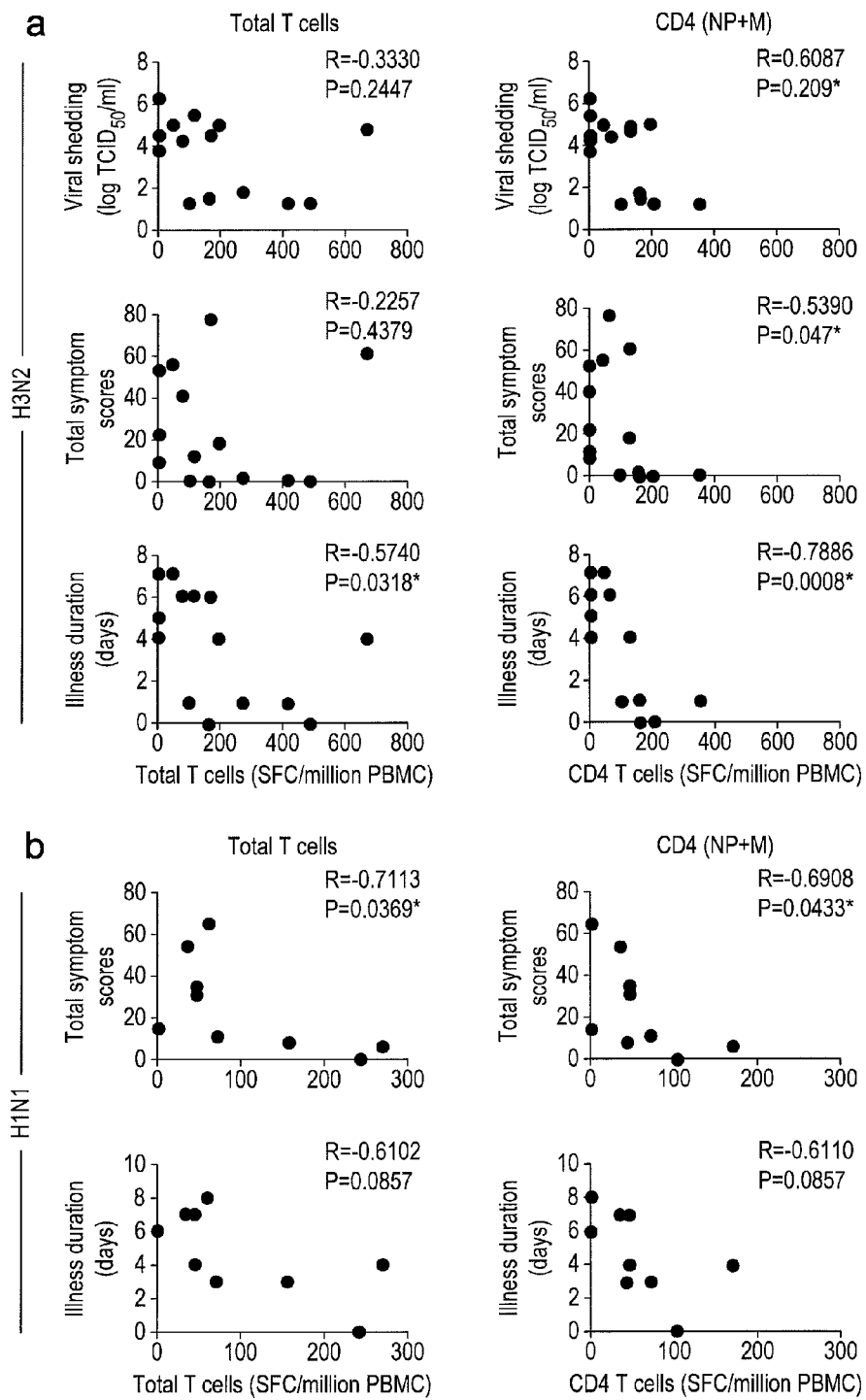
FIG. 6 shows correlations between flu-specific total T and CD4 T cell responses to internal proteins and measure of influenza severity (viral shedding, symptom severity or illness duration) in volunteers infected with (a) H3N2 (WS/67/05) or (b) H1N1 (BR/59/07). Correlations between total symptom scores or length of illness duration against flu-specific total T cell responses or CD4 flu-specific T cells specific to internal proteins including nucleoprotein and matrix of challenge virus. All tests were run by spearman rank correlation test.

As shown in FIG. 6 and Tables 3a and 3b, the magnitude of total pre-existing T cells was strongly correlated with illness duration in H3N2 challenge study (Table 3a, FIG. 6a, r=−0.5740, p=0.0318, Spearman coefficient) and total symptom scores in H1N1 challenge (Table 3b, FIG. 6b, r=−0.7113, p=0.0369, Spearman coefficient,).

TABLE 3a

Correlation of pre-existing CD4 or CD8 cell responses to immunodominant proteins with control of virus shedding and symptom development in H3N2 challenge infection

| Protein | Peak viral load (TCID$_{50}$/ml) | | Symptom scores | | Illness duration (days) | |
|---|---|---|---|---|---|---|
| | Correlation coefficient | P-value | Correlation coefficient | P-value | Correlation coefficient | P-value |
| Total | −0.3330 | 0.2447 | −0.2257 | 0.4379 | −0.5740 | 0.0318 |
| NP and M | −0.4972 | 0.0704 | −0.3402 | 0.2340 | −0.6918 | 0.0061 |
| NP and M (CD4) | −0.6087 | 0.0209 | −0.5390 | 0.0467 | −0.7886 | 0.0008 |
| NP and M (CD8) | 0.0127 | 0.9657 | 0.09640 | 0.7430 | −0.1617 | 0.5808 |

TABLE 3b

Correlation of pre-existing CD4 or CD8 cell responses to influenza proteins with control of virus shedding and symptom development in H1N1 challenge infection

| Protein | Symptom scores | | Illness duration | |
|---|---|---|---|---|
| | Correlation coefficient | P-value | Correlation coefficient | P-value |
| Total | −0.7113 | 0.0369 | −0.6102 | 0.0857 |
| NP and M | −0.852 | 0.0108 | −0.7404 | 0.0255 |
| NP and M (CD4) | −0.6908 | 0.0433 | −0.6110 | 0.0857 |
| NP and M (CD8) | −0.2079 | 0.5809 | −0.1053 | 0.7756 |

When the T cell responses to the immunodominant proteins (NP and M) were examined in detail, it was observed that these protective T cell responses were mediated by pre-existing CD4 (FIG. 6a, right panel; FIG. 6b top right), but not CD8 T cell responses. The observed correlation was independent of the size of flu-specific CD8 response in that the magnitude of pre-existing CD4, but not CD8, cells against the internal proteins NP and M were inversely associated with total symptom scores in both challenge groups. More importantly, virus shedding of H3N2 was predominantly controlled by the level of pre-existing CD4 responses to internal proteins NP and M (r=−0.6087, p=0.0209, Spearman coefficient) but this was not the case for CD8 cells (r=−0.0127, p=0.9657, Spearman coefficient).

To determine the relationship between the acutely expanding T cell population and illness metrics, the relationship between peak T cells on day 7, viral load and symptom severity was determined. The size of the developing acute T cell response correlated positively with viral shedding and illness severity for both models. These findings suggests that pre-existing memory CD4 T cells are the key in the CMI response in limiting illness that once illness is established acutely expanding cell populations tracked peak viral load and thus symptoms.

Phenotypes of Pre-Existing T Cells Against NP and M Flu Proteins

Pre-existing T cell responses against internal protein NP and M as measured by IFN-γ responses were largely CD4 T cell mediated in both H1N1 and H3N2 study groups. In the H3N2 challenge group, 9 subjects had NP and M responses at baseline and 8/9 (89%) had their peptides identified at a single peptide level (Table 4a). For the M protein, 5 out of 8 (63%) peptide responses were CD4 T cell mediated (partial results shown) and for the NP protein, 9 out of 12 (75%) peptide responses were CD4 T cell mediated (results for 9 peptides shown). In the H1N1 challenge group, 7 subjects which were positive with NP and M at baseline and 7/7 (100%) had their peptides identified at a single peptide level (Table 4b). For the M protein, 5 out of 5 (100%) peptides were seen by CD4 T cells (partial results shown) and for the NP protein, 3 out of 6 (50%) peptides were seen by CD4 T cells (partial results shown).

Phenotypes of Induced T Cells Against NP and M Flu Proteins

Figure 7:
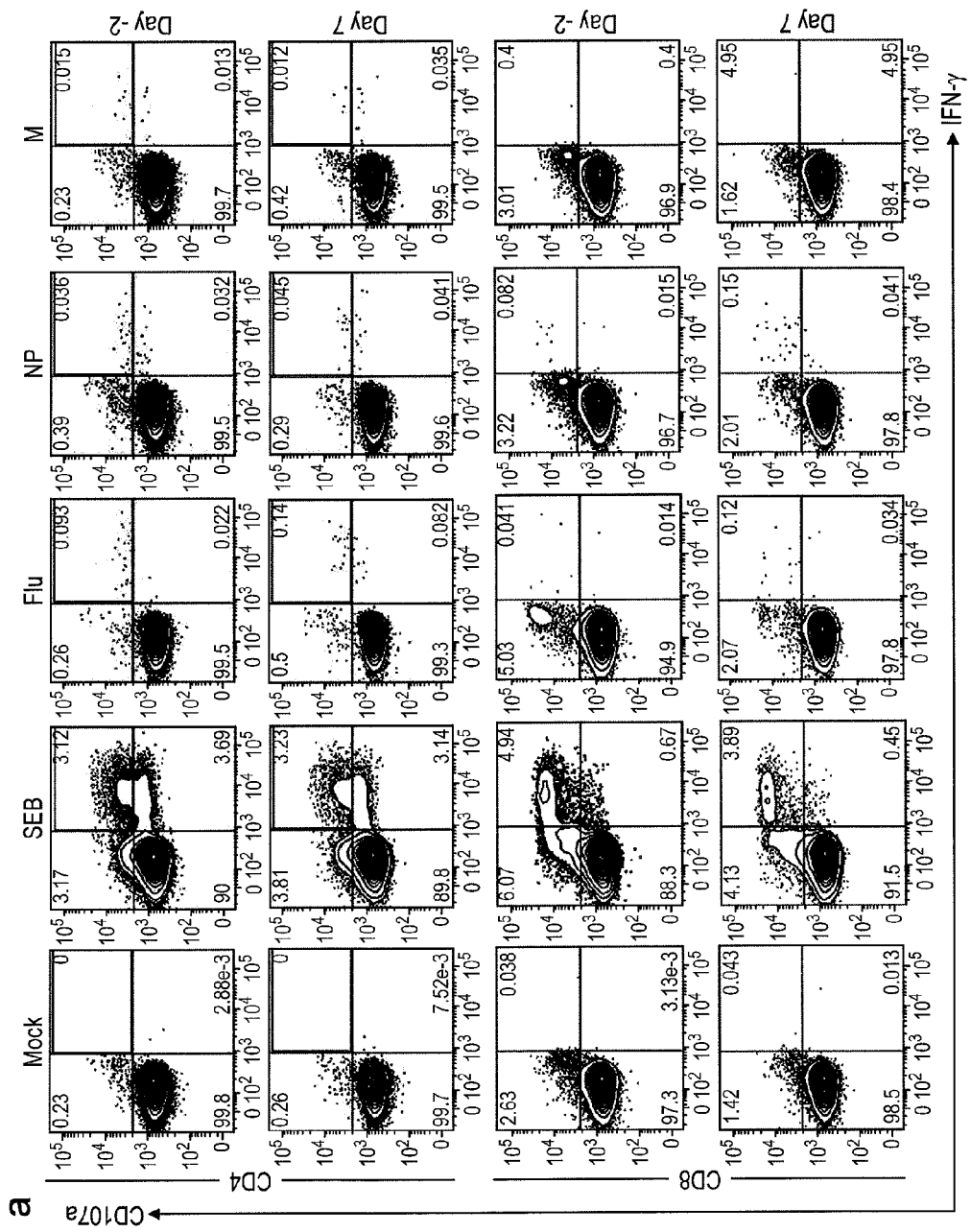
FIG. 7 shows phenotypic and functional studies of CD4 and CD8 cells at baseline and day 7. (a) Expression of IFNγ and CD107a in memory T cells of a representative H3N2 infected subject after stimulation with peptide pools to influenza proteins. PBMC from baseline and day 7 samples were stimulated with different peptide pools (Flu, NP, M) for 6 hours and the ex vivo response was measured by FACS staining. Both memory CD4 and CD8 responses in the same sample were measured. *Staphylococcus* enterotoxin B (SEB) was used as positive control. (b) Killing function of CD4+ T cell lines from the same baseline sample upon recognition of autologous target cells pulsed with peptides was measured by chromium Release Assay. Perforin-dependent cytotoxicity was measured by sensitivity to concanamycin.
Figure 7:
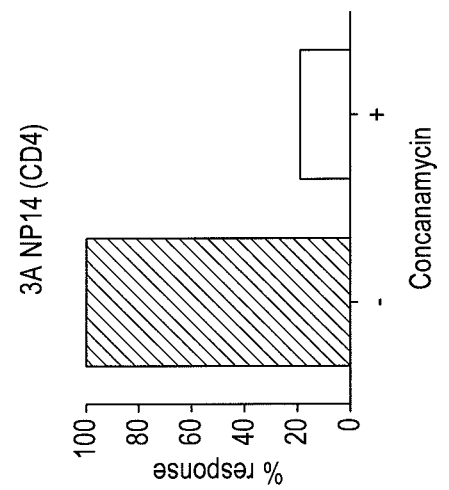
Figure 7:
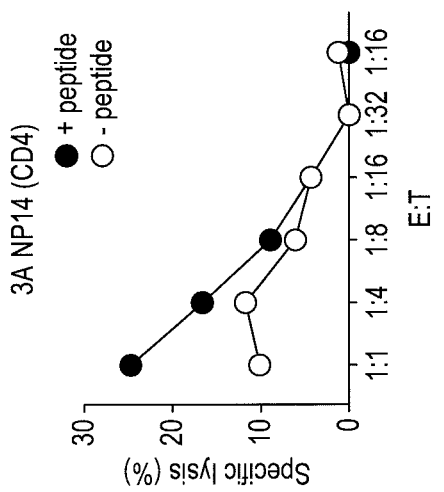
Figure 7:
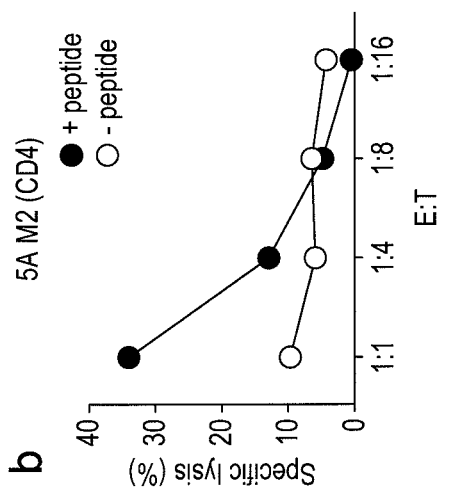

In the day 7 antigen-specific T cell response to NP and M proteins most of the response was by CD4 T cells (Table 5). Upregulation of CD107a expression on memory CD4 T cells was observed following ex vivo stimulation of peptide pools to NP or M proteins (FIG. 7a). Their cytotoxic function was further examined by a Cr-release assay using short-term T cell lines generated from baseline PBMC and on the killing of peptide pulsed autologous B cell lines. As shown in FIG. 7b, these CD4 T cells killed autologous target cells in a peptide specific manner. The killing was sensitive to concanamycin, suggesting cytotoxicity was dependent on the perforin/granzyme pathway. Therefore, these memory CD4 T cells possess a cytotoxic activity as described previously (Cazazza J P et al. J. Exp Med. 203, 2865-77 (2006)).

MHC Class II Expression on Respiratory Epithelium and Changes During Infection

Figure 8:
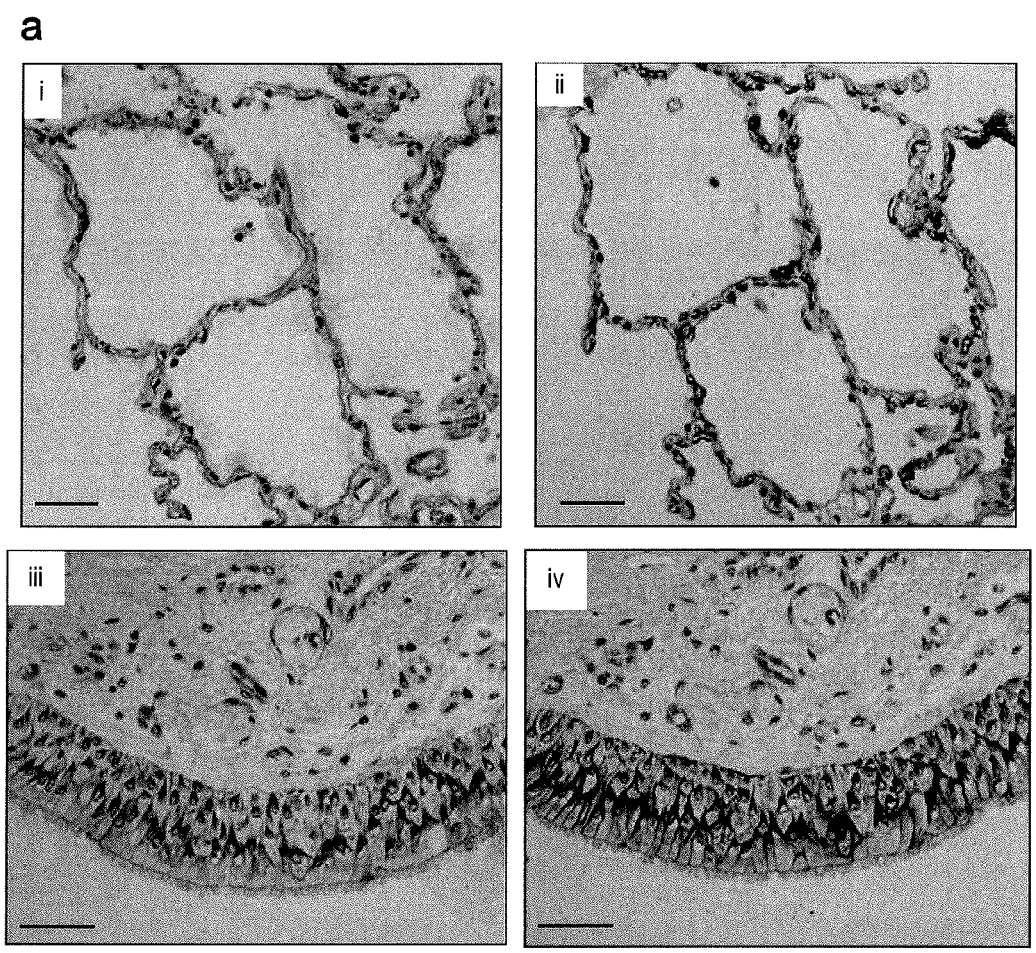
FIG. 8 *a*) Human parenchymal (i) and (ii) and bronchial tissue stained (iii and iv) for MHC II (HLA-DR) 2 mm sequentially cut sections and immunostained using i subtype control monoclonal antibodies (i) and (iii) or antibodies specific for HLA-DR (ii) and (iv) at the same concentration. Signal was amplified using the ABC system, and colour developed using DAB stain. Specific staining is shown in brown, haematoxylin counterstain is shown in blue. Size bar represents 50 um. b) (i) Representative histograms showing specific staining of HLA-DR expression on primary bronchial epithelial cells (PBECs) by flow cytometry using cells incubated in the presence or absence of HLA-DR APCCy7 or IgG2a APCCy7 (isotype). (ii) Graph of mean fluorescence intensity of HLA-DR expression on PBECs using flow cytometry. NT —non treated control, X31 influenza infected cells, UVX31—UV inactivated viral controL HLA-DR is constitutively expressed on primary respiratory epithelial cells, there is a small rise in expression following in vitro infection of these cells with influenza virus which was significant in comparison to stimulation with UV-treated (inactivated) virus. This confirms that respiratory epithelial cells are potential target cells for cytotoxic CD4+ T cells.
Figure 8:
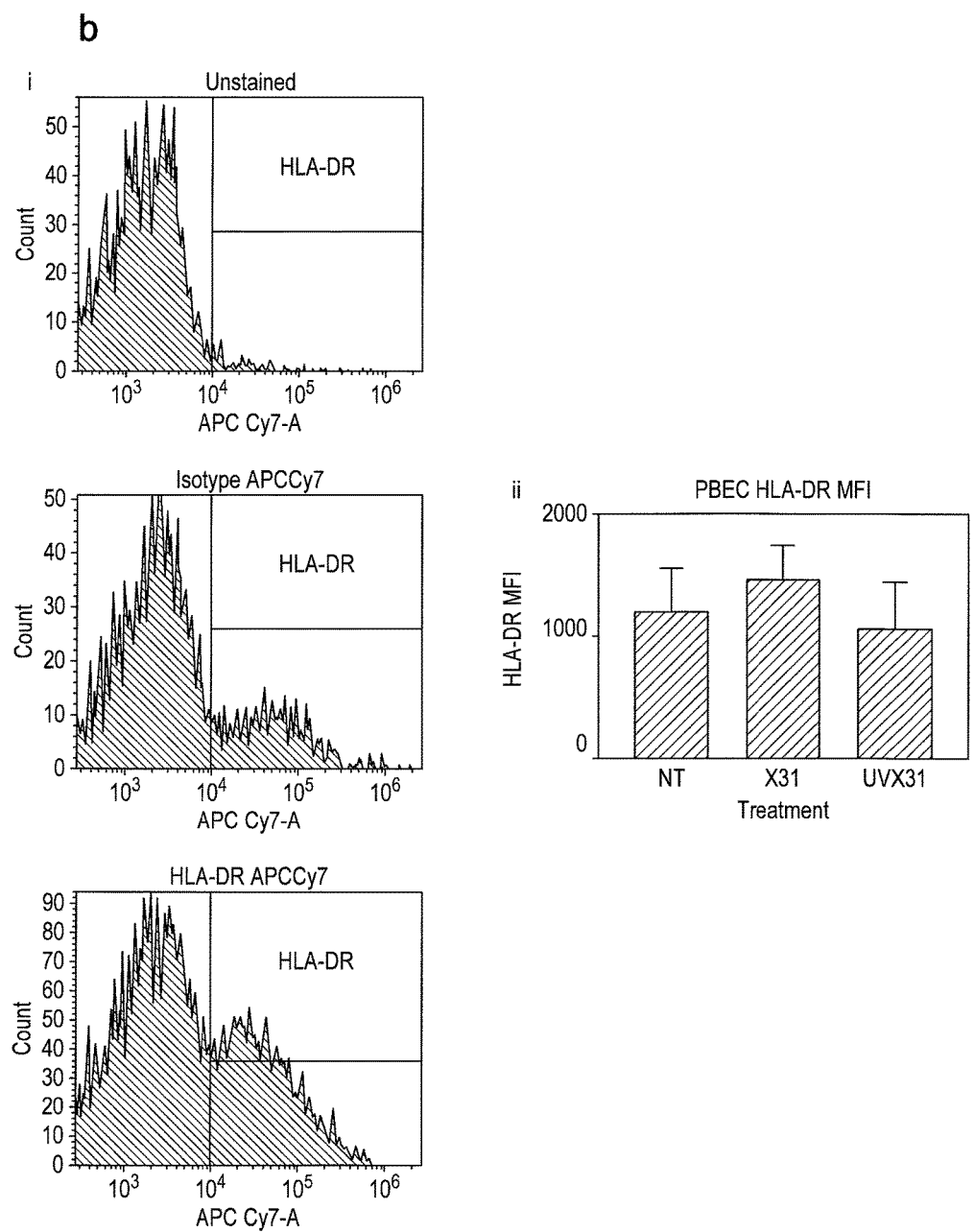

A role for cytotoxic CD4+ cells in limiting viral infection would implicate the need for expression of MHC class II on the respiratory epithelium—the target of influenza infection. To investigate this we analysed the constitutive expression of the MHC class II molecule, HLA-DR, in explanted lung tissue and on primary bronchial epithelial cells in culture (PBECs) and the effect of in vitro influenza infection on expression in PBECs. We found significant constitutive expression of this molecule in both lung tissue and cultured PBECs with a rise in HLA-DR expression after infection of PBECs compared to cells treated with UV-inactivated virus (data in FIG. 8a,b).

TABLE 4a

T cell peptide responses in H3N2 challenge study subjects

| Protein | Peptide ID | Amino acid position | Amino acid sequence | SEQ ID NO | SEQ ID NO in sequence listing | CD4 or CD8 dependency | SFC/million PBMC (range) | Number positive (%) |
|---|---|---|---|---|---|---|---|---|
| M | M15 | 103-119 | LKREITFHKAKEIALSY | 6 | 1 | 4 | 67 (35-96) | 3 (38) |
| M | M23 | 159-175 | HRSHRQMVATTNPLIKH | 7 | 2 | 4 | 158 | 1 (13) |
| M | M25 | 173-189 | IKHENRMVLASTTAKAM | 8 | 3 | 4 | 118 | 1 (13) |
| NP | NP05 | 24-41 | EIRASVGKMIDGIGRFYI | 9 | 4 | 4 | 141.5 (35-248) | 2 (26) |
| NP | NP08 | 48-65 | KLSDHEGRLIQNSLTIEK | 10 | 5 | 4 | 26 | 1 (13) |
| NP | NP14 | 95-111 | PIYRRVDGKWMRELVLY | 11 | 6 | 4 | 113 (45-181) | 2 (26) |
| NP | NP15 | 102-119 | GKWMRELVLYDKEEIRRI | 12 | 7 | 4 | 93 (45-141) | 2 (26) |
| NP | NP20 | 141-156 | SNLNDATYQRTRALVR | 14 | 8 | 8 | 391 | 1 (13) |
| NP | NP21 | 147-163 | TYQRTRAVLRTGMDPRM | 15 | 9 | 8 | 331 | 1 (13) |
| NP | NP32 | 229-246 | KFQTAAQRAMVDQVRESR | 18 | 10 | 8 | 104 | 1 (13) |
| NP | NP57 | 404-420 | GQTSVQPTFSVQRNLPF | 19 | 11 | 4 | 10 | 1 (13) |
| NP | NP58 | 411-428 | TFSVQRSLPFEKSTIMAA | 20 | 12 | 4 | 10 | 1 (13) |

TABLE 4b

T cell peptides responses in H1N1 challenge study subjects

| Protein | Peptide ID | Amino acid position | Amino acid sequence | SEQ ID NO | SEQ ID NO in sequence listing | CD4 or CD8 dependency | SFC/million PBMC (range) | Positive no (%) |
|---|---|---|---|---|---|---|---|---|
| M | M13 | 97-114 | VKLYRKLKREITFHGAKE | 23 | 13 | 4 | 41 (30-52) | 2 (28) |
| NP | NP09 | 65-82 | RMVLSAFDERRNKYLEEH | 26 | 14 | 4 | 38 | 1 (14) |
| NP | NP27 | 209-226 | GENGRKTRIAYERMCNIL | 29 | 15 | 8 | 30 | 1 (14) |
| NP | NP28 | 217-234 | IAYERMCNILKGKFQTAA | 30 | 16 | 8 | 40 | 1 (14) |
| NP | NP52 | 409-426 | QPTFSVQRNLPFDKTTIM | 31 | 17 | 4 | 26 | 1 (14) |

TABLE 5

T cell responses to H1N1 challenge study

| Subjects | Peptide ID | Amino acid position | Amino acid sequence | SEQ ID NO | SEQ ID NO in sequence listing | CD4 or CD8 dependency | SFC/million PBMC Days after challenge | | |
|---|---|---|---|---|---|---|---|---|---|
| | | | | | | | -2 | 7 | 28 |
| B017(2C) | NP52 | 409-426 | QPTFSVQRNLPFDKTTIM | 31 | 17 | 4 | 26 | 76 | 10 |
| B017(2C) | M13 | 97-114 | VKLYRKLKREITFHGAKE | 23 | 13 | 4 | 52 | 316 | 33 |
| B005 (15C) | NP27 | 209-226 | GENGRKTRIAYERMCNIL | 29 | 15 | 8 | 30 | 157 | 10 |
| B005 (15C) | NP28 | 217-234 | IAYERMCNILKGKFQTAA | 30 | 16 | 8 | 40 | 67 | 10 |
| B005 (15C) | M13 | 97-114 | VKLYRKLFREITFHHAKE | 23 | 13 | 4 | 30 | 70 | 10 |
| B005 (20C) | NP09 | 65-82 | RMVLSAFDERRNKYLEEH | 26 | 14 | 4 | 38 | 187 | 113 |

The invention claimed is:

1. A method for screening a plurality of test peptides having a level of identity with a sequence of a protein of a virus, to identify any peptide or peptides which are capable of ameliorating infection by the virus in a human, the method comprising:

a) obtaining T0 samples comprising T cells from at least five different human test subjects who are seronegative for antibodies to the virus, where each of the T0 samples is obtained from a single human test subject, b) contacting the T cells in each of the T0 samples with the plurality of test peptides, quantifying the level of response of the T cells in each of the T0 samples to each of the test peptides, and identifying any peptide or peptides which induce a T cell response in one or more of the T0 samples, c) inoculating and infecting each one of the at least five human test subjects with the virus after obtaining the T0 sample from the subject in step a), d) obtaining a measure of disease severity in each one of the at least five human test subjects following infection with the virus in step c);

e) for each peptide identified in step b), correlating the level of response to the peptide of the T cells in each T0 sample with the measure of disease severity in the test subject from whom the T0 sample was obtained and f) for any one peptide where an inverse correlation is found in step e), identifying the peptide as a peptide that is capable of ameliorating infection by the virus in a human subject.

2. The method of claim 1, wherein the subjects have not been vaccinated against the virus with a vaccine designed to elicit a T cell response.

3. The method of claim 1, wherein the measure of disease severity is i) a score of severity of symptoms of the viral infection experienced by the subjects, ii) a measure of viral shedding or viral load in the test subjects, iii) duration of illness experienced by the test subjects, iv) a measure of a biomarker typically increased during infection with the virus, or v) a measure of a biomarker typically decreased during infection with the virus.

4. The method of claim 1, wherein the peptide is about 7to about 25 amino acids long.

5. The method of claim 4, wherein the peptide is 9-25 amino acids or 10-20 amino acids and preferably 15-18 amino acids long.

6. The method of claim 1, wherein the peptide has at least 70% identity with a sequence of a viral protein.

7. The method of claim 6, wherein the peptide has at least 80% identity with a sequence of a viral protein, optionally wherein the peptide is identical a sequence of a viral protein.

8. The method of claim 1, wherein a library of peptides is screened.

9. The method of claim 8, wherein the library of peptides spans a protein of a viral proteome.

10. The method of claim 1, wherein the peptide is synthetic.

11. The method of claim 1, wherein the virus is capable of causing acute, self-limiting infection in humans.

12. The method of claim 1, wherein the virus is a respiratory virus, an enteric virus or a mucosal virus, or a virus that infects by the mucosal route.

13. The method of claim 1, wherein the virus is an enteric virus, optionally the virus is norovirus.

14. The method of claim 1, wherein the virus a) is a virus from the Orthomyxoviridae, Paramyxoviridae, Coronaviridae, Picornaviridae, Caliciviridae, Flaviviridae or Reoviridae families, or b) is a respiratory virus, optionally the virus is selected from an influenza virus, rhinovirus or respiratory syncytial virus, human metapneumovirus, adenovirus, coronavirus, boca virus or other acute respiratory virus, preferably the virus is selected from an influenza virus, rhinovirus or respiratory syncytial virus.

15. The method of claim 14, wherein the virus is an influenza virus, optionally an influenza A virus.

16. The method of claim 9, wherein the library of peptides spans the protein nucleoprotein (NP) and/or matrix (M1 or M2) protein of influenza virus.

17. The method of claim 1, wherein CD4+T cell responses are quantified.

18. The method of claim 1, wherein the test samples comprising T cells are obtained from more than 10, 15 or 20 different subjects.

19. The method of claim 1, wherein the peptide is a polypeptide, an oligopeptide or a protein.

20. The method of claim 1, further comprising the step, prior to collecting the T0 test samples, of placing the at least five human test subjects into controlled conditions in isolation.

* * * * *

SEQUENCE LISTING

<160> NUMBER OF SEQ ID NOS: 17

<210> SEQ ID NO 1
<211> LENGTH: 17
<212> TYPE: PRT
<213> ORGANISM: Influenza A virus

<400> SEQUENCE: 1

Leu Lys Arg Glu Ile Thr Phe His Gly Ala Lys Glu Ile Ala Leu Ser
1               5                   10                  15

Tyr

<210> SEQ ID NO 2
<211> LENGTH: 17
<212> TYPE: PRT
<213> ORGANISM: Influenza A virus

<400> SEQUENCE: 2

His Arg Ser His Arg Gln Met Val Ala Thr Thr Asn Pro Leu Ile Lys
1               5                   10                  15

His

<210> SEQ ID NO 3
<211> LENGTH: 17
<212> TYPE: PRT
<213> ORGANISM: Influenza A virus

<400> SEQUENCE: 3

Ile Lys His Glu Asn Arg Met Val Leu Ala Ser Thr Thr Ala Lys Ala
1               5                   10                  15

Met

<210> SEQ ID NO 4
<211> LENGTH: 18
<212> TYPE: PRT
<213> ORGANISM: Influenza A virus

<400> SEQUENCE: 4

Glu Ile Arg Ala Ser Val Gly Lys Met Ile Asp Gly Ile Gly Arg Phe
1               5                   10                  15

Tyr Ile

```
<210> SEQ ID NO 5
<211> LENGTH: 18
<212> TYPE: PRT
<213> ORGANISM: Influenza A virus

<400> SEQUENCE: 5

Lys Leu Ser Asp His Glu Gly Arg Leu Ile Gln Asn Ser Leu Thr Ile
1               5                   10                  15

Glu Lys

<210> SEQ ID NO 6
<211> LENGTH: 17
<212> TYPE: PRT
<213> ORGANISM: Influenza A virus

<400> SEQUENCE: 6

Pro Ile Tyr Arg Arg Val Asp Gly Lys Trp Met Arg Glu Leu Val Leu
1               5                   10                  15

Tyr

<210> SEQ ID NO 7
<211> LENGTH: 18
<212> TYPE: PRT
<213> ORGANISM: Influenza A virus

<400> SEQUENCE: 7

Gly Lys Trp Met Arg Glu Leu Val Leu Tyr Asp Lys Glu Glu Ile Arg
1               5                   10                  15

Arg Ile

<210> SEQ ID NO 8
<211> LENGTH: 16
<212> TYPE: PRT
<213> ORGANISM: Influenza A virus

<400> SEQUENCE: 8

Ser Asn Leu Asn Asp Ala Thr Tyr Gln Arg Thr Arg Ala Leu Val Arg
1               5                   10                  15

<210> SEQ ID NO 9
<211> LENGTH: 17
<212> TYPE: PRT
<213> ORGANISM: Influenza A virus

<400> SEQUENCE: 9

Thr Tyr Gln Arg Thr Arg Ala Leu Val Arg Thr Gly Met Asp Pro Arg
1               5                   10                  15

Met

<210> SEQ ID NO 10
<211> LENGTH: 18
<212> TYPE: PRT
<213> ORGANISM: Influenza A virus

<400> SEQUENCE: 10

Lys Phe Gln Thr Ala Ala Gln Arg Ala Met Val Asp Gln Val Arg Glu
1               5                   10                  15

Ser Arg

<210> SEQ ID NO 11
```

<211> LENGTH: 17
<212> TYPE: PRT
<213> ORGANISM: Influenza A virus

<400> SEQUENCE: 11

Gly Gln Thr Ser Val Gln Pro Thr Phe Ser Val Gln Arg Asn Leu Pro
1 5 10 15

Phe

<210> SEQ ID NO 12
<211> LENGTH: 18
<212> TYPE: PRT
<213> ORGANISM: Influenza A virus

<400> SEQUENCE: 12

Thr Phe Ser Val Gln Arg Asn Leu Pro Phe Glu Lys Ser Thr Ile Met
1 5 10 15

Ala Ala

<210> SEQ ID NO 13
<211> LENGTH: 18
<212> TYPE: PRT
<213> ORGANISM: Influenza A virus

<400> SEQUENCE: 13

Val Lys Leu Tyr Arg Lys Leu Lys Arg Glu Ile Thr Phe His Gly Ala
1 5 10 15

Lys Glu

<210> SEQ ID NO 14
<211> LENGTH: 18
<212> TYPE: PRT
<213> ORGANISM: Influenza A virus

<400> SEQUENCE: 14

Arg Met Val Leu Ser Ala Phe Asp Glu Arg Arg Asn Lys Tyr Leu Glu
1 5 10 15

Glu His

<210> SEQ ID NO 15
<211> LENGTH: 18
<212> TYPE: PRT
<213> ORGANISM: Influenza A virus

<400> SEQUENCE: 15

Gly Glu Asn Gly Arg Lys Thr Arg Ile Ala Tyr Glu Arg Met Cys Asn
1 5 10 15

Ile Leu

<210> SEQ ID NO 16
<211> LENGTH: 18
<212> TYPE: PRT
<213> ORGANISM: Influenza A virus

<400> SEQUENCE: 16

Ile Ala Tyr Glu Arg Met Cys Asn Ile Leu Lys Gly Lys Phe Gln Thr
1 5 10 15

Ala Ala

<210> SEQ ID NO 17
<211> LENGTH: 18

```
<212> TYPE: PRT
<213> ORGANISM: Influenza A virus

<400> SEQUENCE: 17

Gln Pro Thr Phe Ser Val Gln Arg Asn Leu Pro Phe Asp Lys Thr Thr
1               5                   10                  15

Ile Met
```